United States Patent
Takeda

(10) Patent No.: US 10,119,881 B2
(45) Date of Patent: Nov. 6, 2018

(54) METHOD AND APPARATUS FOR DETECTING GAS LEAKAGE FROM RADIOACTIVE MATERIAL SEALED CONTAINER

(71) Applicant: CENTRAL RESEARCH INSTITUTE OF ELECTRIC POWER INDUSTRY, Tokyo (JP)

(72) Inventor: Hirofumi Takeda, Chiba (JP)

(73) Assignee: CENTRAL RESEARCH INSTITUTE OF ELECTRIC POWER INDUSTRY, Tokyo (JP)

( * ) Notice: Subject to any disclaimer, the term of this patent is extended or adjusted under 35 U.S.C. 154(b) by 493 days.

(21) Appl. No.: 15/266,346

(22) Filed: Sep. 15, 2016

(65) Prior Publication Data

US 2017/0074744 A1    Mar. 16, 2017

(30) Foreign Application Priority Data

Sep. 16, 2015    (JP) ................................. 2015-182926

(51) Int. Cl.
| | | |
|---|---|---|
| *G21F 5/00* | (2006.01) | |
| *G21F 5/012* | (2006.01) | |
| *G21F 5/06* | (2006.01) | |
| *G21C 13/00* | (2006.01) | |
| *F25D 3/00* | (2006.01) | |
| *G01M 3/00* | (2006.01) | |
| *G01N 25/72* | (2006.01) | |

(52) U.S. Cl.
CPC ............ *G01M 3/002* (2013.01); *G01N 25/72* (2013.01)

(58) Field of Classification Search
CPC .......... G01K 17/00; G01K 1/14; G01K 13/00; G01K 15/007; G01K 1/026; G01K 7/04; G21F 5/12; B65D 83/38; G01N 25/72
USPC ............ 374/4, 137, 208, 141, 54; 250/506.1
See application file for complete search history.

(56) References Cited

U.S. PATENT DOCUMENTS

| | | | | |
|---|---|---|---|---|
| 3,073,961 A | * | 1/1963 | Nachbar ................... | G21F 5/10 250/506.1 |
| 3,229,096 A | * | 1/1966 | Bonilla ................... | G21F 5/005 250/507.1 |
| 4,437,578 A | * | 3/1984 | Bienek ...................... | G21F 5/12 220/288 |
| 8,410,946 B2 | * | 4/2013 | Ansari .................. | G01M 3/002 340/605 |

(Continued)

FOREIGN PATENT DOCUMENTS

| | | | | |
|---|---|---|---|---|
| EP | | 1492385 A2 * | 12/2004 | ............ H05B 3/746 |
| JP | | 2002202400 A | 7/2002 | |

(Continued)

*Primary Examiner* — Gail Kaplan Verbitsky
(74) *Attorney, Agent, or Firm* — The Webb Law Firm

(57) ABSTRACT

A method for detecting gas leakage from a radioactive material sealed container includes measuring a temperature at a top portion of a metallic sealed container, a temperature at a bottom portion of a lid portion of a concrete-made storage container facing the top portion of the metallic sealed container, or a temperature of a member existing between the bottom portion of the lid portion and the top portion of the metallic sealed container. An inner temperature of the lid portion of the concrete-made storage container is also measured. Presence of leakage of inactive gas is estimated by comparing the temperatures.

15 Claims, 21 Drawing Sheets

(56) References Cited

U.S. PATENT DOCUMENTS

| | | | |
|---|---|---|---|
| 2005/0145633 A1* | 7/2005 | Goto | A47J 36/06 |
| | | | 220/573.4 |
| 2011/0215936 A1* | 9/2011 | Ansari | G01M 3/002 |
| | | | 340/584 |
| 2015/0059445 A1* | 3/2015 | Tragsdorf | G21F 5/12 |
| | | | 73/49.2 |
| 2017/0108396 A1* | 4/2017 | Takeda | G01M 3/002 |
| 2018/0073163 A1* | 3/2018 | Higashi | C30B 25/12 |
| 2018/0130565 A1* | 5/2018 | Lehnert | G21F 5/012 |

FOREIGN PATENT DOCUMENTS

| | | |
|---|---|---|
| JP | 2004077124 A | 3/2004 |
| JP | 2004226385 A | 8/2004 |
| JP | 2005265443 A | 9/2005 |

\* cited by examiner

METHOD AND APPARATUS FOR DETECTING GAS LEAKAGE FROM RADIOACTIVE MATERIAL SEALED CONTAINER

CROSS-REFERENCE TO RELATED APPLICATION

This application claims priority to Japanese Patent Application No. 2015-182926 filed Sep. 16, 2015, the disclosure of which is hereby incorporated in its entirety by reference.

BACKGROUND

Technical Field

The present invention relates to a method and an apparatus for detecting gas leakage from a radioactive material sealed container. More specifically, the present invention particularly relates to a method and an apparatus for detecting leakage of inactive gas such as helium filled in a metallic canister of a concrete cask.

Related Art

A concrete cask has been a focus of constant attention as a storage means for high radioactive material represented by spent nuclear fuel in a nuclear reactor. The concrete cask is formed of: a cylindrical sealed container made of stainless steel and having a structure that stores spent fuel and seals the same by welding (hereinafter referred to as canister); and a non-sealed concrete-made storage container that has a shielding function and houses the canister (hereinafter referred to as concrete container). The concrete cask is a dry storage facility adapted to remove decay heat of spent fuel contained inside the canister by naturally convecting external air through an air ventilation port provided at upper and lower portions of the concrete container.

The canister has a sealed structure obtained by welding so as not to leak sealed radioactive material to the outside, and also adapted to transfer the decay heat of the spent fuel contained inside the canister via helium to the canister by sealing helium that is inactive gas having thermal conductivity higher than air. Therefore, in the event of helium leakage, there may be a concern that contamination caused by leakage of the radioactive material and insufficient heat removal of the decay heat occur.

In the case of assuming that the concrete cask is installed near coast, cooling air contains salt. Therefore, there may be a concern that a sealing function of the canister is lost by stress corrosion cracking. Additionally, in the case of storing the concrete cask in an inland area also, a deterioration/degradation problem cannot be entirely ignored in consideration of long-term storage, and there may be a concern that helium sealed inside the canister leaks due to a defect, corrosion, and the like at a welding portion of the canister.

A phenomenon of helium leakage is an event to be avoided because radioactive material may be emitted to the environment. Therefore, in the event of such a phenomenon, immediately detecting the event and taking countermeasures are needed. Accordingly, development of a technology to detect helium leakage at an early stage is demanded.

In response to this demand, there is a proposed method of detecting helium leakage, in which a temperature difference between a center temperature at a bottom portion and a center temperature at a top portion in a canister is monitored, and in the case where the temperature difference is increased and a feeding air temperature is decreased, occurrence of gas leakage is determined (JP 2005-265443 A).

However, according to the technology disclosed in JP 2005-265443 A, since it is necessary to measure the temperatures at two points of the top portion and the bottom portion of the canister housed inside the concrete container, construction work for installing thermocouples at the two points of the top portion and the bottom portion of the cask is required. However, depending on a structure of an air inlet port of the concrete cask, the construction work to directly install the thermocouple at the bottom portion of the canister may be difficult.

SUMMARY

The present invention is directed to providing a method and an apparatus for detecting gas leakage from a canister as a radioactive material sealed container, in which presence of leakage of inactive gas can be detected by utilizing only a peripheral temperature of a canister top portion.

A method for detecting gas leakage from a radioactive material sealed container corresponding to a mode to implement the technical idea of the present invention is a method for detecting leakage of inactive gas from a metallic sealed container of the radioactive material sealed container that includes: the metallic sealed container adapted to store and seal spent fuel and the inactive gas; and a non-sealed concrete-made storage container having a shielding function and adapted to store the metallic sealed container. The method includes:

measuring a temperature at a top portion of the metallic sealed container, a temperature at a bottom portion of a lid portion of the concrete-made storage container facing the top portion of the metallic sealed container, or a temperature of a member existing between the bottom portion of the lid portion and the top portion of the metallic sealed container;

also measuring an inner temperature of the lid portion of the concrete-made storage container; and estimating presence of leakage of the inactive gas by comparing the temperature at the top portion of the metallic sealed container with the inner temperature of the lid portion of the concrete-made storage container or comparing the inner temperature of the lid portion of the concrete-made storage container with the temperature at the bottom portion of the lid portion of the concrete-made storage container or the temperature of the member existing between the bottom portion of the lid portion and the top portion of the metallic sealed container.

An apparatus for detecting gas leakage from a radioactive material sealed container corresponding to a mode to implement the technical idea of the present invention is an apparatus for detecting leakage of inactive gas from a metallic sealed container of the radioactive material sealed container that includes: the metallic sealed container adapted to store and seal spent fuel and the inactive gas; and a non-sealed concrete-made storage container having a shielding function and adapted to store the metallic sealed container. The apparatus includes:

a first temperature sensor adapted to measure a temperature at a top portion of the metallic sealed container, a temperature at a bottom portion of a lid portion of the concrete-made storage container facing the top portion of the metallic sealed container, or a temperature of a member existing between the bottom portion of the lid portion and the top portion of the metallic sealed container;

a second temperature sensor adapted to measure an inner temperature of the lid portion of the concrete-made storage container; and a gas leakage estimation unit adapted to estimate presence of leakage of the inactive gas by comparing a temperature measured by the first temperature sensor with a temperature measured by the second temperature sensor.

According to the above-described method and the apparatus for detecting gas leakage from a radioactive material sealed container, leakage of filled gas such as helium from the metallic sealed container can be determined only from temperature information in the periphery of the top portion of the metallic sealed container. Therefore, temperature sensor installation work is required only at one place on the top portion side of the metallic sealed container, and construction is simpler compared to the case of installing thermocouples at two places of the top portion and the bottom portion of the metallic sealed container. Especially, construction work for installing the thermocouple at the bottom portion of the metallic sealed container is not needed in the concrete-made storage container including a stepwise air inlet port on a side surface in the periphery of the bottom portion. Therefore, it is much more advantageous in viewpoint of construction work.

DETAILED DESCRIPTION

Figure 1:
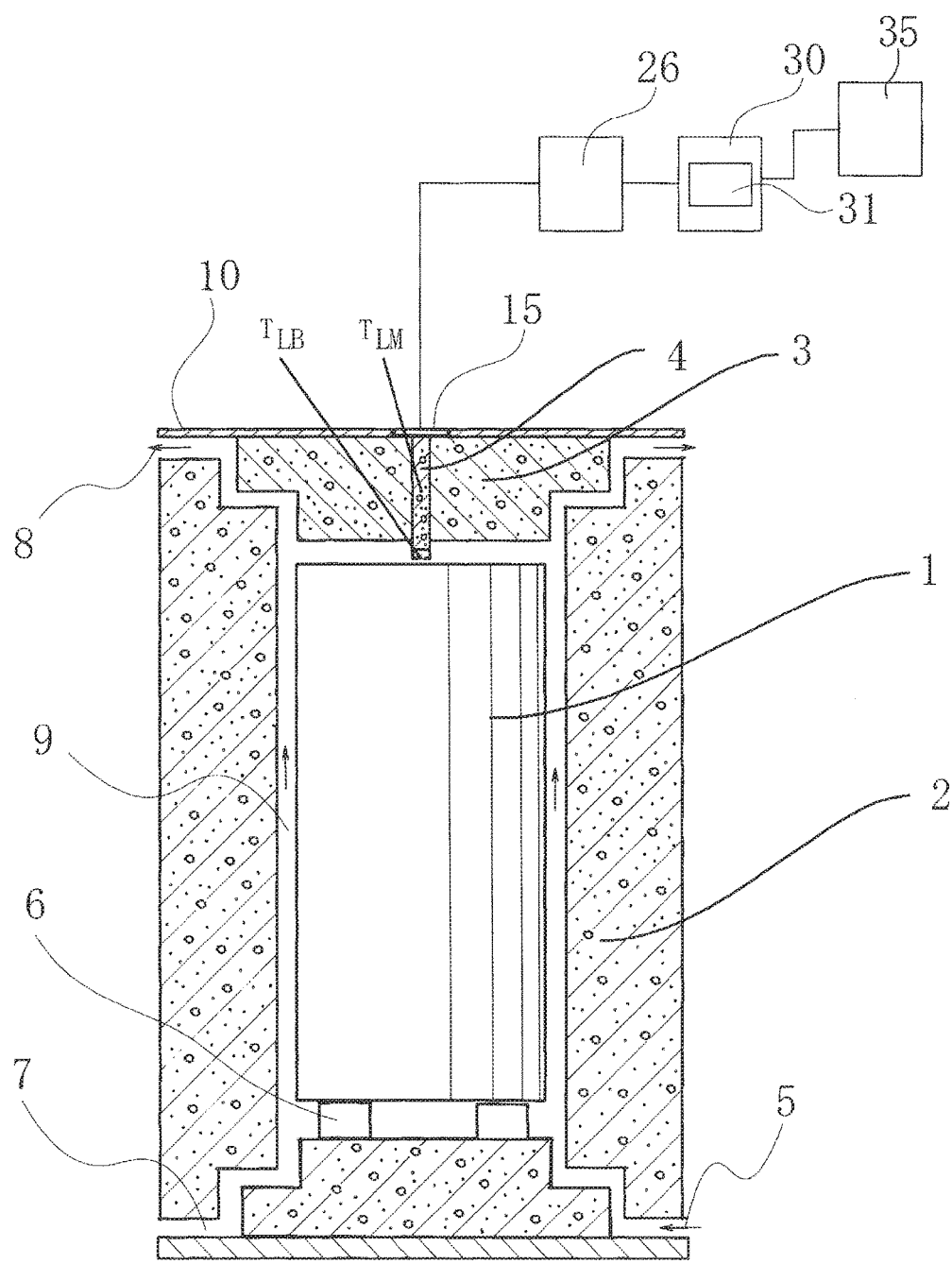
FIG. 1 is a schematic diagram illustrating an embodiment of a method and an apparatus for detecting gas leakage from a radioactive material sealed container according to the present invention.

In the following, an embodiment as an exemplary aspect to implement a technical idea of the present invention will be described in detail using the drawings. In the present embodiment, exemplified is a case where an apparatus for detecting gas leakage is applied to a radioactive material sealed container illustrated in FIG. 1. However, a structure, a shape, quality of material, and the like of the radioactive material sealed container in which the present invention is applied are not limited to the example illustrated in FIG. 1.

The radioactive material sealed container of the present embodiment is a concrete-made dry cask or simply called a concrete cask, and formed of: a metallic sealed container having a structure adapted to store and seal spent fuel by welding (hereinafter referred to as a canister 1); and a non-sealed concrete-made storage container having a shielding function and adapted to house the canister 1 (hereinafter referred to as a concrete container 2). The radioactive material sealed container of the present embodiment has a structure in which decay heat of the spent fuel contained inside the canister 1 is removed by naturally convecting external air 5 via an air inlet port 7 and an outlet port 8 which are air ventilation ports provided at upper and lower portions of the concrete container 2.

The canister 1 is supported by a supporting leg 6, and forms a flow passage 9 in a space with the concrete container 2 around the canister.

Meanwhile, a bar-shaped thermometer 4 is embedded in a lid portion of the concrete container 2 (hereinafter simply referred to as a concrete lid 3).

The concrete lid 3 is basically formed of concrete as a main constituent material in order to shield neutrons in the same manner as the concrete container 2.

Figure 2:
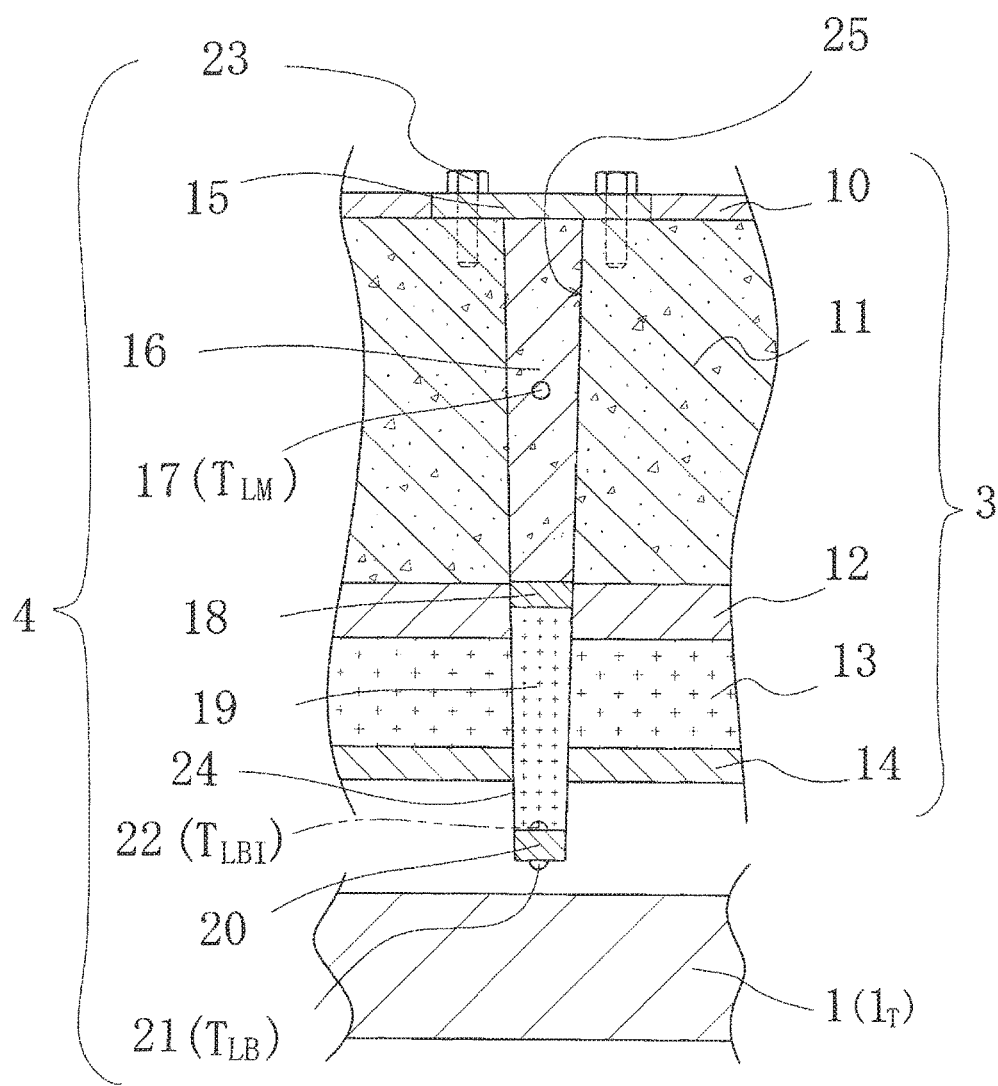
FIG. 2 is an enlarged cross-sectional view illustrating a concrete lid, a canister lid, and temperature sensors.

For example, as illustrated in FIG. 2, the concrete lid 3 has a shielding structure formed by sequentially stacking, from the top, a metal plate 10 to be an outer shell, a concrete material 11, a metal plate 12 to be a partition, a heat insulator 13, and a metal plate 14 to be an outer shell on a bottom side. A bottom portion of the concrete lid 3 represents the metal plate 14 in the case of the present embodiment. In the following, the bottom portion of the concrete lid 3 is described as the bottom portion 14 of the concrete lid 3.

The canister 1 is generally made of metal such as stainless steel and formed as a cylindrical sealed container by welding. The canister 1 generally has a double lid and is sealed by welding after the container containing a radioactive material and a space between an inner lid and an outer lid are filled with inactive gas, but may also have a single lid depending on circumstances. Therefore, in the present embodiment, a top portion of the canister 1 (hereinafter referred to as a canister top portion $1_T$) means a lid portion of the canister 1 facing the concrete lid 3.

As the gas sealed inside the canister 1, for example, helium (He) is preferable. Helium is the inactive gas having thermal conductivity higher than air. The present invention can be implemented under negative pressure, but heat of the radioactive material is transmitted to the canister 1 and heat removal performance may be improved by making helium to positive pressure. Furthermore, helium may also be kept at high pressure in order to improve heat removal performance, and for example, in a case implemented in United States, helium is kept at about 8 atmospheric pressure.

Note that filled gas is not necessarily limited to helium, and other inactive gases having the thermal conductivity higher than air may also be used as well. In this case, the adopted inactive gas is to be a detecting target.

Figure 4C:
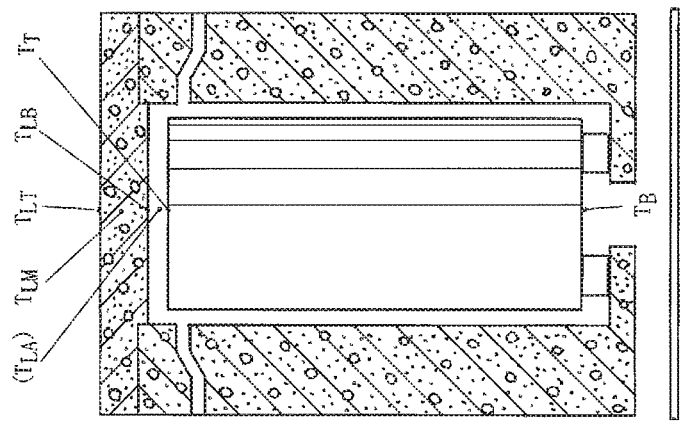
FIG. 4C is a schematic drawing of a concrete cask used in helium leakage tests made of reinforced concrete and having an air inlet port at a bottom portion (Case 3)
Figure 4B:
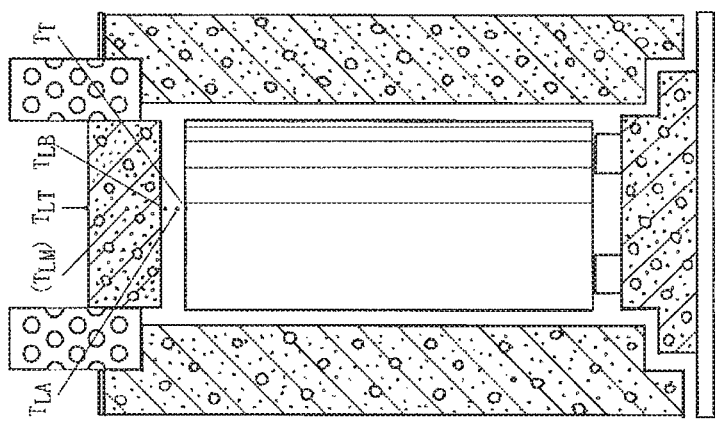
FIG. 4B is a schematic drawing of a concrete cask used in helium leakage tests made of a steel plate (concrete filled steel) and having an air inlet port on a bottom portion side surface using a lid having outlet ducts with low flow resistance (Case 2)
Figure 4A:
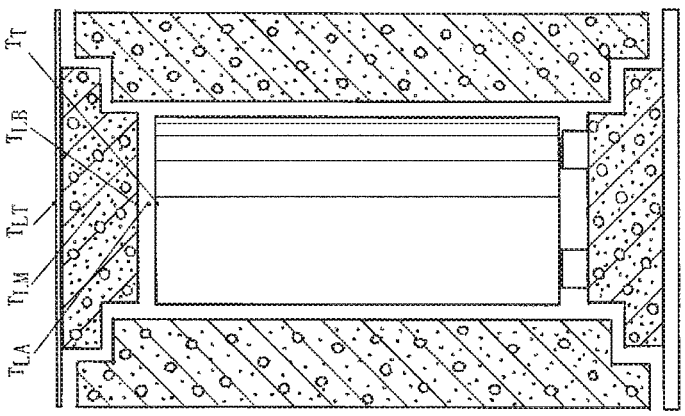
FIG. 4A is a schematic drawing of a concrete cask used in helium leakage tests made of a steel plate (concrete filled steel) and having an air inlet port on a bottom portion side surface (Case 1)
Figure 5:
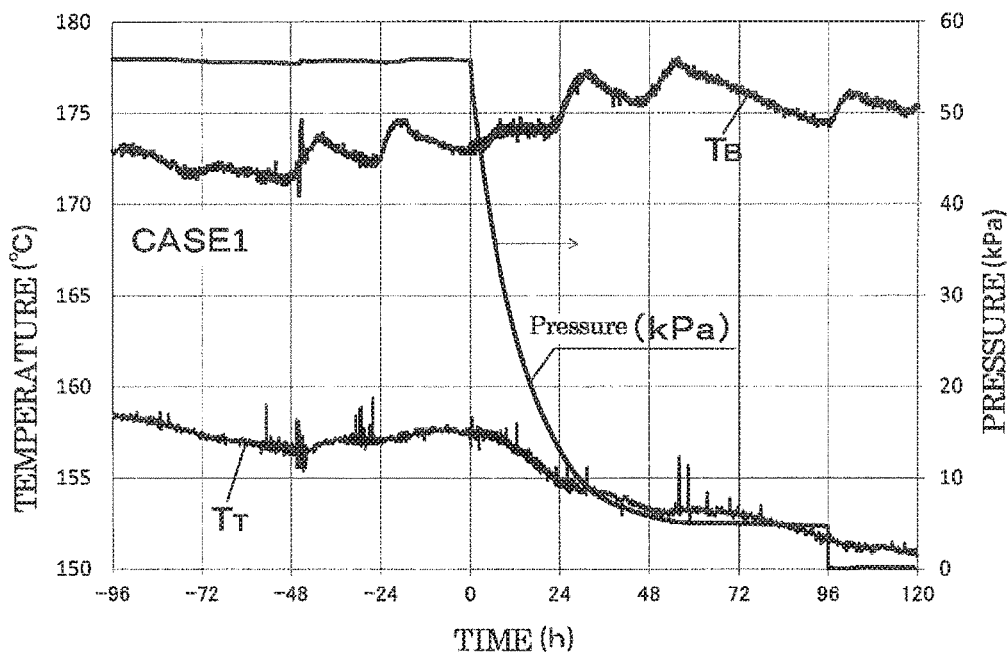
FIG. 5 is a graph illustrating change of a canister top portion center temperature $T_T$ and change of a canister bottom portion center temperature $T_B$ relative to inner pressure of a canister before and after helium leakage in Case 1.

Meanwhile, the structure of the concrete cask may be a concrete cask made of a steel plate (CFS: concrete filled steel) illustrated in FIG. 4A, a concrete cask made of CFS using a lid having outlet ducts with low flow resistance illustrated in FIG. 4B, or a concrete cask made of reinforced concrete (RC) illustrated in FIG. 4C.

Furthermore, a form of an air inlet port may be a stepwise shape as illustrated in FIGS. 4A and 4B or a cross groove shape as illustrated in FIG. 4C. The air inlet port having the cross groove shape is formed of: a cross-shaped groove that passes a center of a bottom portion of the concrete container 2; and a vertical hole penetrating the inside of the container at an intersecting portion with the groove.

Additionally, as for cooling fluids to be introduced into the concrete container 2, the external air is directly made to flow inside in the present embodiment, but depending on circumstances, air that has been adjusted to have a predetermined temperature range and humidity or a cooling gas other than air may also be fed inside.

The apparatus for detecting gas leakage according to the present embodiment applied to the above-described concrete cask includes: a first temperature sensor 21 adapted to measure a canister top portion temperature $T_T$ that is a surface temperature of the canister top portion $\mathbf{1}_T$, a temperature $T_{LB}$ of the bottom portion 14 of the concrete lid 3 facing the canister top portion $\mathbf{1}_T$, or a temperature $T_{LBI}$ of a member existing between the bottom portion 14 of the concrete lid 3 and the canister top portion $\mathbf{1}_T$; a second temperature sensor 17 adapted to measure a lid inner temperature $T_{LM}$ of the concrete lid 3 facing the canister top portion $\mathbf{1}_T$; and, a gas leakage estimation unit 31 adapted to estimate presence of inactive gas leakage by comparing a measured temperature of the first temperature sensor 21 with a measured temperature of the second temperature sensor 17. In other words, when significant fluctuation between the measured temperatures of the first temperature sensor 21 and the second temperature sensor 17 are recognized, it is estimated that inactive gas leakage has occurred.

Here, at the time of monitoring leakage determination data, a difference between two temperatures is preferably used in viewpoint of easy evaluation. For example, it may be considered to calculate, as a change amount, a difference between each of average temperatures of the two temperatures during a period deemed as proper operation time without occurrence of helium leakage or each of the two temperatures at a specific time point deemed as the proper operation time (referred to as reference temperature) and each of the two temperatures at the time of measurement, and then further obtain and monitor a difference between these change amounts. In this case, when the difference between the temperature change amounts tends to increase, it can be determined that leakage is occurring.

Furthermore, in the case of directly comparing actual measurement temperatures of the two temperatures $T_T$ and $T_{LM}$ or actual measurement temperatures of the temperatures $T_{LB}$ and $T_{LM}$, when the temperature difference between both temperatures tends to be reduced, it can be determined that leakage is occurring. Furthermore, in the case of displaying two actual measurement temperatures to be compared also, the two actual measurement temperatures are multiply displayed, making the respective comparing average values of the two actual measurement temperatures the same. Consequently, when a deviation state in a graph illustrating changes of temperatures of both temperatures tends to be enlarged, it can be determined that leakage is occurring.

Preferably, the first temperature sensor 21 directly measures the canister top portion temperature $T_T$ in terms of improving inactive gas leakage detection sensitivity. However, in the case of making a temperature sensor such as a thermocouple contact the canister top portion $\mathbf{1}_T$ directly, there may be problems such as galvanic corrosion caused by the canister 1 contacting a different kind of metal, and damage/degradation of the temperature sensor by radioactive rays.

On the other hand, in a method of measuring the temperature at the canister top portion $\mathbf{1}_T$ with a radiation thermometer from above a penetration hole opened at the concrete lid 3, there may be a problem such as damage of the shielding function because it is necessary to enlarge a diameter of the penetration hole in order to enable adjustment of a focal point of the radiation thermometer. Therefore, this method is not realistic.

To solve the above-described problem, the inventor has found that temperature information having high correlation with the canister top portion temperature $T_T$ and excellently reflected with change of the canister top portion temperature $T_T$ can be obtained by measuring a temperature of a member that receives influence of the canister top portion temperature $T_T$ by using a contact type thermometer such as a thermocouple or a thermistor, without causing corrosion of the canister 1 and damage/degradation of the temperature sensor 21. Furthermore, the inventor made it clear, from experiments/analysis, that the temperature information not only having high correlation with the canister top portion temperature $T_T$ but also having temperature value close thereto can be obtained by measuring, with the contact type thermometer such as the thermocouple or the thermistor, a temperature of a member such as the metal plate 20 made to project close to the canister top portion $\mathbf{1}_T$ from the metal plate 14 corresponding to the bottom portion of the concrete lid 3 as illustrated in FIG. 2.

Here, it is not important to grasp an exact temperature in measuring the canister top portion temperature $T_T$, and it is important to grasp movement of temperature change. Considering this, the inventor has found substituting, for the canister top portion temperature $T_T$, the temperature of the metal plate 20 located at a tip of the bar-shaped thermometer 4 installed at a position closest to the surface of the canister top portion $\mathbf{1}_T$.

Therefore, in the present embodiment, as the temperature of the member that receives influence of the canister top portion temperature $T_T$, the temperature $T_{LB}$ at the bottom portion 14 of the concrete lid 3 facing the canister top portion $\mathbf{1}_T$ or the temperature $T_{LBI}$ of the member existing between the bottom portion 14 of the concrete lid 3 and the canister top portion $\mathbf{1}_T$ is measured.

The member that receives influence of the canister top portion temperature $T_T$ is a member heated by radiation from the canister top portion $\mathbf{1}_T$. As the member that receives influence of the surface temperature $T_T$ of the canister top portion $\mathbf{1}_T$, more specifically, the metal plate corresponding to the bottom portion 14 of the concrete lid 3 and a metal component projecting to the canister top portion $\mathbf{1}_T$ side more than the bottom portion 14 may be exemplified.

In the present embodiment, the metal plate 20 located at the tip of the bar-shaped thermometer 4 projecting toward the canister top portion $\mathbf{1}_T$ from the bottom portion 14 of the concrete lid 3 is adopted as the member that receives influence of the canister top portion temperature $T_T$.

In the description of the present invention, a temperature of the member that receives influence of the canister top portion temperature $T_T$ including the bottom portion 14 of the concrete lid 3 is described as a lid bottom portion temperature $T_{LB}$ for convenience of the description. More specifically, the temperature $T_{LB}$ at the bottom portion 14 of the concrete lid 3 and the temperature $T_{LBI}$ of the member existing between the bottom portion 14 of the concrete lid 3 and the canister top portion $\mathbf{1}_T$ are described as the lid bottom portion temperature $T_{LB}$.

The second temperature sensor 17 measures a temperature at a portion that hardly receives influence of the canister top portion temperature $T_T$ inside the concrete lid 3. In the description of the present invention, the temperature at a portion that hardly receives influence of the canister top portion temperature $T_T$ inside the concrete lid 3 is described as a lid inner temperature $T_{LM}$.

In the present embodiment, the lid inner temperature $T_{LM}$ corresponds to a temperature at the concrete 11 of the concrete lid 3.

In the present embodiment, the bar-shaped thermometer 4 including the first temperature sensor 21 and the second temperature sensor 17 is used. Furthermore, the bar-shaped thermometer 4 is inserted into the relatively small penetration hole 25 opened at the concrete lid 3, thereby providing the first temperature sensor 21 at the bottom portion of the concrete lid 3 and also providing the second temperature sensor 17 inside the concrete lid 3.

The first temperature sensor 21 and the second temperature sensor 17 are installed on a vertical line passing a center in a diameter direction of the canister top portion $1_T$ and the concrete lid 3, namely, on a center axis. Temperature change at the canister top portion $1_T$ in the event of helium leakage is largest at the center position of the canister top portion $1_T$. Therefore, by monitoring the temperature at the center position of the canister top portion $1_T$, detection sensitivity can be improved, and furthermore, it is expected that highly reliable gas leakage detection can be performed.

However, accurately arranging the respective temperature sensors 17, 21 on the center axis is not an indispensable condition, and the temperature sensors may also be arranged at a position distant from the center, such as a position close to an edge of the canister top portion $1_T$ or the concrete lid 3. Furthermore, the respective temperature sensors 17, 21 may also be arranged on a different vertical axis line.

The first temperature sensor 21 provided at the tip of the bar-shaped thermometer 4 measures the temperature at the metal plate 20 as the member that receives influence of the surface temperature of the canister top portion $1_T$.

In the case of the present embodiment, the first temperature sensor 21 is provided on a front surface, i.e. an undersurface, of the metal plate 20 facing the canister top portion $1_T$ and measures the lid bottom portion temperature $T_{LB}$.

However, depending on circumstances, the first temperature sensor 22 may be arranged on a back surface, i.e. an upper surface, of the metal plate 20 facing the heat insulator 19 as indicated by a virtual line in FIG. 2, and may also measure a back surface temperature $T_{LBI}$ of the metal plate 20. In this case, the first temperature sensor 22 is prevented from being damaged by radioactive rays because the metal plate 20 functions as a metallic protection cover and shields the radioactive rays such as γ-rays. Furthermore, the back surface temperature $T_{LBI}$ of the metal plate 20 is little different from the front surface temperature $T_{LB}$ of the metal plate 20, and may also be used as a substitute of the top portion temperature $T_T$ of the metallic sealed container.

As the respective temperature sensors 17, 21 or 22, for example, preferably the thermometer such as a thermocouple or a thermistor is used. In this case, in addition to a merit that the structure is simple and inexpensive, long-term stable operation can be expected because of the simple structure. These two temperature sensors 17, 21 or 22 are electrically connected to a temperature measurement device 26, and temperature measurement is performed by utilizing thermoelectromotive force provided by a Seebeck effect.

The bar-shaped thermometer 4 is formed by sequentially stacking, from the top, a metal plate 15 to be a lid, a concrete 16, a metal plate 18, the heat insulator 19, and the metal plate 20 to be the bottom as illustrated in FIG. 2, and formed to have a shielding structure in the same manner as the concrete lid 3 by a peripheral surface of the bar-shaped thermometer being coated with a metallic protection cylinder 24 and covered with a lid using the metal plate 15.

Furthermore, the bar-shaped thermometer 4 includes the thermocouple 17 as the second temperature sensor 17 inside the concrete 16 and also includes the thermocouple 21 as the first temperature sensor 21 on the front surface of the metal plate 20. Therefore, the first temperature sensor 21 and the second temperature sensor 17 are arranged at desired positions of the concrete lid 3 just by closing the penetration hole 25 of the concrete lid 3 by inserting the bar-shaped thermometer 4 into the penetration hole 25, and furthermore, the shielding function of the concrete lid 3 can be maintained and a stagnation space under the concrete lid 3 is secured, and detection sensitivity can be more improved.

Moreover, since a space between the canister 1 and lid 3 of the concrete container 2 is narrow and forms the stagnation space to provide a heat insulation effect, the top portion temperature $T_T$ of the canister 1 hardly receives influence of the feeding air temperature $T_{IN}$, and also hardly receives influence of daily fluctuation of the feeding air temperature $T_{IN}$. Therefore, since leakage of the filled gas from the canister 1, such as helium, can be determined only from the temperature information in the periphery of the top portion of the canister 1, complicated determination considering daily fluctuation of an external air temperature is not needed, and reliability of detection is improved.

Meanwhile, the concrete 16 of the bar-shaped thermometer 4 has a thickness same as the concrete 11 of the concrete lid 3. Furthermore, in the case of the present embodiment, the thickness of the heat insulator 19 of the bar-shaped thermometer 4 is made equal to or more than that of the heat insulator 13 of the concrete lid 3. Consequently, the metal plate 20 and the first temperature sensor 21 provided at the tip of the bar-shaped thermometer 4 can be arranged closer to the canister top portion $1_T$ than the concrete lid bottom portion 14. Additionally, the metallic protection cylinder 24 is preferably formed of material having high heat conductivity.

The bar-shaped thermometer 4 is inserted into the penetration hole 25 of the concrete lid 3 and then fixed by fastening the concrete lid 3 and the metal plate 15 of the bar-shaped thermometer 4 with a bolt 23. Therefore, only by simple construction work such as providing the penetration hole on the lid portion of the concrete-made storage container, inserting the bar-shaped thermometer into the penetration hole, and then fix the same with the bolt, the second temperature sensor is arranged inside the lid portion of the concrete-made storage container and also the first temperature sensor can be arranged in a range from the bottom portion of the lid portion of the concrete-made storage container to the top portion of the metallic sealed container. Moreover, since the bar-shaped thermometer 4 can be detached from the concrete lid 3 just by removing the bolt 23 even in the case where the thermocouple 21 is deteriorated by radioactive rays, replacement work is simple when the temperature sensors 17, 21 or 22 is out of order.

Additionally, in the case of the present embodiment, the bar-shaped thermometer 4 and the penetration hole 25 of the concrete lid 3 into which the thermometer 4 is inserted are both formed in tapered shapes, and have structures in which both peripheral surfaces closely contact each other in a state that the first temperature sensor 21 provided at the tip of the bar-shaped thermometer 4 is located close to the canister top portion $1_T$ to an extent not contacting the canister top portion $1_T$.

In this case, since the outer peripheral surface of the protection cylinder 24 of the bar-shaped thermometer 4 closely contacts an inner peripheral surface that defines the penetration hole 25, an air layer is not formed between the concrete lid 3 and the bar-shaped thermometer 4 and a heat insulation effect is prevented from being generated. Therefore, the temperature of the concrete 16 of the bar-shaped thermometer 4 can follow temperature change inside the concrete 11 of the concrete lid 3, and the temperature of the concrete 16 can be treated as the lid inner temperature $T_{LM}$.

Needless to mention, a relation between the bar-shaped thermometer 4 and the penetration hole 25 of the concrete lid 3 may be a relation between a straight bar and a straight through hole. Even in this case also, the temperature of the concrete 11 of the concrete lid 3 can be reflected on the concrete 16 of the bar-shaped thermometer 4 by closing clearance between the bar-shaped thermometer 4 and the concrete lid 3 by filling mortar and the like.

According to the experiments by the inventor, when helium leakage occurs from the inside of the canister 1, the surface temperature $T_T$ of the canister top portion $1_T$ starts decreasing, and the inner temperature $T_{LM}$ of the concrete lid 3 changes with a time lag from the change of the surface temperature $T_T$ of the canister top portion $1_T$ and also gradually decreases compared to a decrease rate of the surface temperature $T_T$ of the canister top portion $1_T$. Based on this fact, the inventor has found that: when helium leakage occurs from the inside of the canister 1, a difference between the surface temperature $T_T$ of the canister top portion $1_T$ and the inner temperature $T_{LM}$ of the concrete lid 3 changes; and this change tends to be enlarged.

Additionally, as described above, by measuring the temperature of the bottom portion 14 of the concrete lid 3 or the temperature of the member existing between the bottom portion 14 and the canister top portion $1_T$ and receiving influence of the canister top portion temperature $T_T$, namely, the lid bottom portion temperature $T_{LB}$, even the thermocouple or the thermistor can measure a temperature having sufficiently high correlation with the surface temperature of the canister top portion $1_T$ in a non-contacting state.

For example, it is found that the temperature $T_{LB}$ of the metal plate 20 measured by the first temperature sensor 21 becomes almost same value as the canister top portion temperature $T_T$, namely $T_{LB} \approx T_T$, by setting, close to a position about 10 mm from the surface of the canister top portion $1_T$, the first temperature sensor 21 adapted to measure the temperature of the metal plate 20 located at the tip of the bar-shaped thermometer 4.

Accordingly, measured temperature data of the first temperature sensor 21 or 22 and the second temperature sensor 17 output from the temperature measurement device 26 are taken into, for example, the gas leakage estimation unit 31 formed inside an apparatus 30 that detects gas leakage, and change of the temperature difference between the lid inner temperature $T_{LM}$ and the canister top portion temperature $T_T$ is displayed on a display device 35 to enable comparison and monitoring. Alternatively, when there is significant fluctuation in the temperature difference, it is determined that leakage of the inactive gas is occurring, and a message indicating this fact is displayed, or various warning actions such as warning sound, warning light emission, and the like can be executed.

Here, decay heat of spent fuel inside the canister is reduced with passage of years, and therefore, the canister top portion temperature $T_T$ decreases even without occurrence of inactive gas leakage. A decreased temperature of the canister top portion temperature $T_T$ caused by reduction of decay heat with age (hereinafter referred to as decreased temperature $T_d$ with age) is, for example, about 1° C. per year according to the experiments by the inventor. However, in the case where leakage is little, this may be a factor of detection error. Therefore, discriminating the factor is preferable.

Accordingly, preferably, the decreased temperature $T_d$ with age caused by the reduction of decay heat is considered as an allowable value in the present invention.

Additionally, a maximum decreased temperature of the canister top portion temperature $T_T$ caused by helium leakage (hereinafter referred to as maximum decreased temperature $T_{Ld}$ at the time of gas leakage) also decreases along with decrease of the canister top portion temperature $T_T$ caused by the reduction of decay heat.

Therefore, the apparatus for detecting gas leakage according to the present embodiment is adapted to consider reduction of decay heat caused by passage of storage period.

Here, the apparatus for detecting gas leakage may be formed by a dedicated device including respective units to execute predetermined processing, or may be implemented by a computer executing a program.

Figure 29:
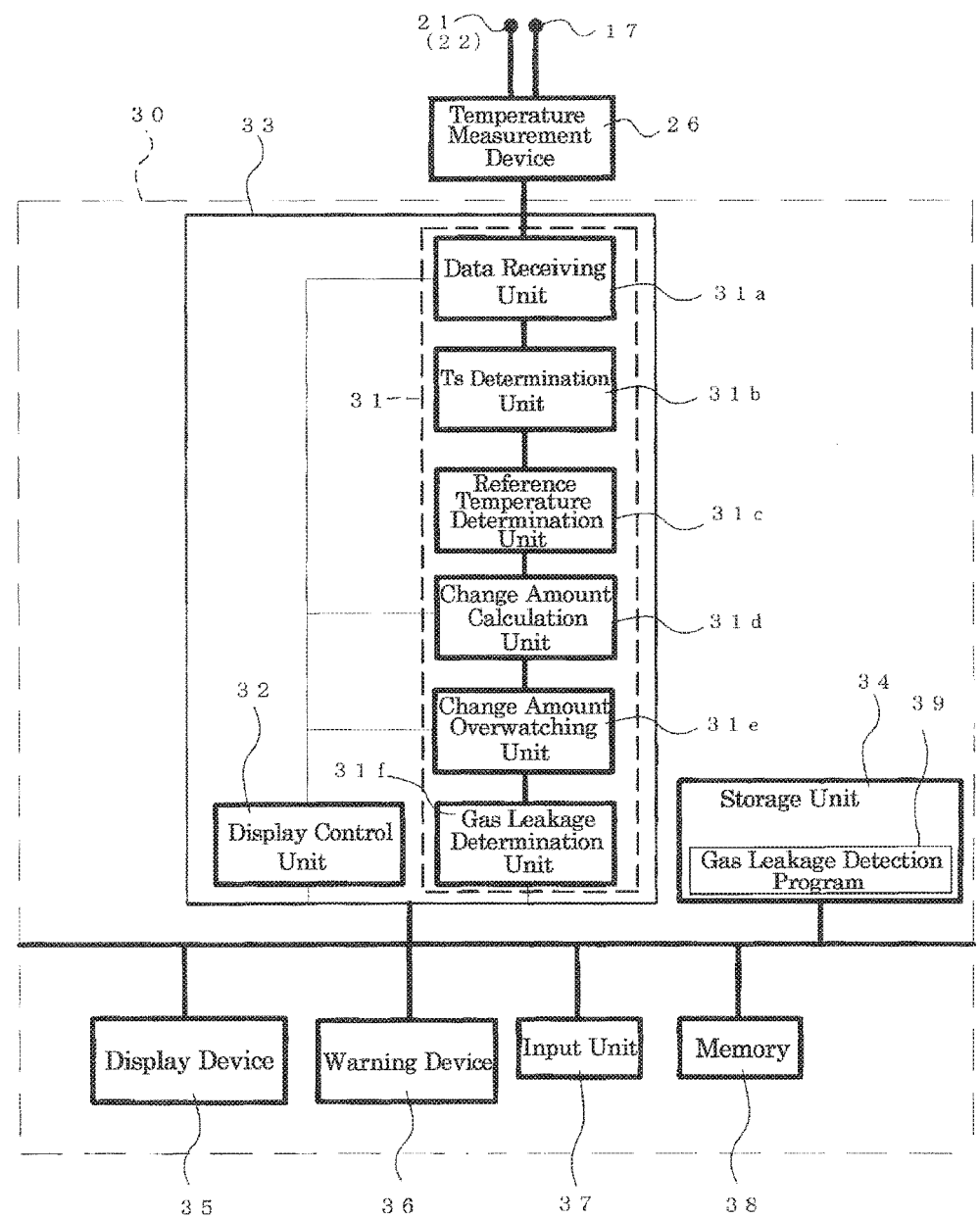
FIG. 29 is a functional block diagram illustrating an embodiment of the apparatus for detecting gas leakage from a radioactive material sealed container according to the present invention.

For example, in an example illustrated in FIG. 29, a gas leakage detection program 39 stored in a storage unit 34 is executed, thereby implementing the apparatus for detecting gas leakage by a computer 30. However, the apparatus for detecting gas leakage may also be formed as the dedicated device 30 including respective units such as a data receiving unit 31a and the like to execute predetermined processing, a display control unit 32, and so on.

The apparatus for detecting gas leakage according to the present embodiment has the gas leakage estimation unit 31 that includes: a data receiving unit 31a adapted to read the canister top portion temperature $T_T$ or the temperature $T_{LB}$ of the member that receives influence of the canister top portion temperature $T_T$ as a substitute temperature thereof, and the lid inner temperature $T_{LM}$ from the temperature measurement device 26 including the first temperature sensor 21 and the second temperature sensor 17; a Ts determination unit 31b adapted to calculate a threshold temperature Ts to determine occurrence of gas leakage; a reference temperature determination unit 31c adapted to determine, as reference temperatures, average values of respective measured temperatures or temperatures at certain time points at the time or during a period deemed as a proper operation state without gas leakage; a change amount calculation unit 31d adapted to calculate differences $\delta T_T$ or $\delta T_{LB}$, and $\delta T_{LM}$ from the respective reference temperatures of the respective measured temperatures (hereinafter referred to as change amounts of the measured temperatures); a change amount monitoring unit 31e adapted to calculate and monitor a difference $\delta(T_{LM}-T_T)$ or a difference $\delta(T_{LM}-T_{LB})$ between change amounts of the measured temperatures from the reference temperatures (hereinafter referred to as difference between change amounts); and a gas leakage determination unit 31f adapted to determine occurrence of gas leakage when the difference between change amounts $\delta(T_{LM}-T_T)$ or $\delta(T_{LM}-T_{LB})$ is larger than the threshold temperature Ts.

Meanwhile, in the present embodiment, exemplified is the case of adopting the lid bottom portion temperature $T_{LB}$ as the substitute temperature of the canister top portion temperature $T_T$ because the temperature at the tip of the bar-shaped thermometer 4 set closest to the canister top portion $1_T$, specifically, the lid bottom portion temperature $T_{LB}$ measured by the first temperature sensor 21 in FIG. 2 is almost the same value as the canister top portion temperature $T_T$. In this point, the above-described and the mentioned below canister top portion temperature $T_T$ may also be described as the lid bottom portion temperature $T_{LB}$.

However, in the case of directly measuring the canister top portion temperature $T_T$ itself with a non-contact type temperature sensor or the like, this temperature may also be used. Furthermore, even when the canister top portion temperature $T_T$ and the lid bottom portion temperature $T_{LB}$, are not almost the same values, in the case where there is high correlation between both temperatures, the lid bottom portion temperature $T_{LB}$ may also be used.

Additionally, the apparatus for detecting gas leakage according to the present embodiment includes the display control unit 32 adapted to constantly display, on the display device 35, the change amounts $\delta T_{LM}$ and $\delta T_T$ from the respective reference temperatures of the respective measured temperatures and/or fluctuation of a change amount difference therebetween $\delta(T_{LM}-T_T)$. Note that reference sign 33 in the drawing indicates a control unit (central processing device), reference sign 36 a warning device, reference sign 37 an input unit, and reference sign 38 a memory respectively.

Ts determination unit 31b calculates the maximum decreased temperature $T_{Ld}$ at the time of gas leakage and the decreased temperature $T_d$ with age, and determines the threshold temperature Ts adapted to determine occurrence of gas leakage within a range between the maximum decreased temperature $T_{Ld}$ at the time of gas leakage and the decreased temperature $T_d$ with age. In other words, the threshold temperature Ts is an index in order to determine whether a difference between the canister top portion temperature $T_T$ and the inner temperature $T_{LM}$ or a difference between the lid bottom portion temperature $T_{LB}$ and the inner temperature $T_{LM}$ indicates significant fluctuation.

In the case where the threshold temperature Ts is set to a value close to, for example, the decreased temperature $T_d$ with age, the value is included in a fluctuation band in normal operation time, and this may cause a determination error such as leakage occurrence in spite of a fact that inactive gas is not actually leaking. On the other hand, in the case where the threshold temperature Ts is set to a value close to, for example, the maximum decreased temperature $T_{Ld}$ at the time of gas leakage, there may be a concern that abnormality is overlooked. Therefore, the threshold temperature Ts is preferably set to a temperature lower than the maximum decreased temperature $T_{Ld}$ at the time of gas leakage and higher than the decreased temperature $T_d$ with age, for example, an intermediate value therebetween or a value close the intermediate value.

Here, the maximum decreased temperature $T_{Ld}$ at the time of gas leakage is attributable to a phenomenon caused by convection change inside the canister at the time of leakage. Therefore, it is not easy to calculate the maximum decreased temperature $T_{Ld}$ at the time of gas leakage because calculation is complicated. Accordingly, a database for test results accumulated in heat removal tests and leakage tests per concrete cask type may be preliminarily prepared, and the threshold temperature Ts may also be determined by calculating an optimal temperature based on the database. Needless to mention, the maximum decreased temperature $T_{Ld}$ at the time of gas leakage may also be acquired by calculation.

For example, the maximum decreased temperature $T_{Ld}$ at the time of gas leakage and the decreased temperature $T_d$ with age can be estimated from decay heat analysis results and test results.

Figure 35:
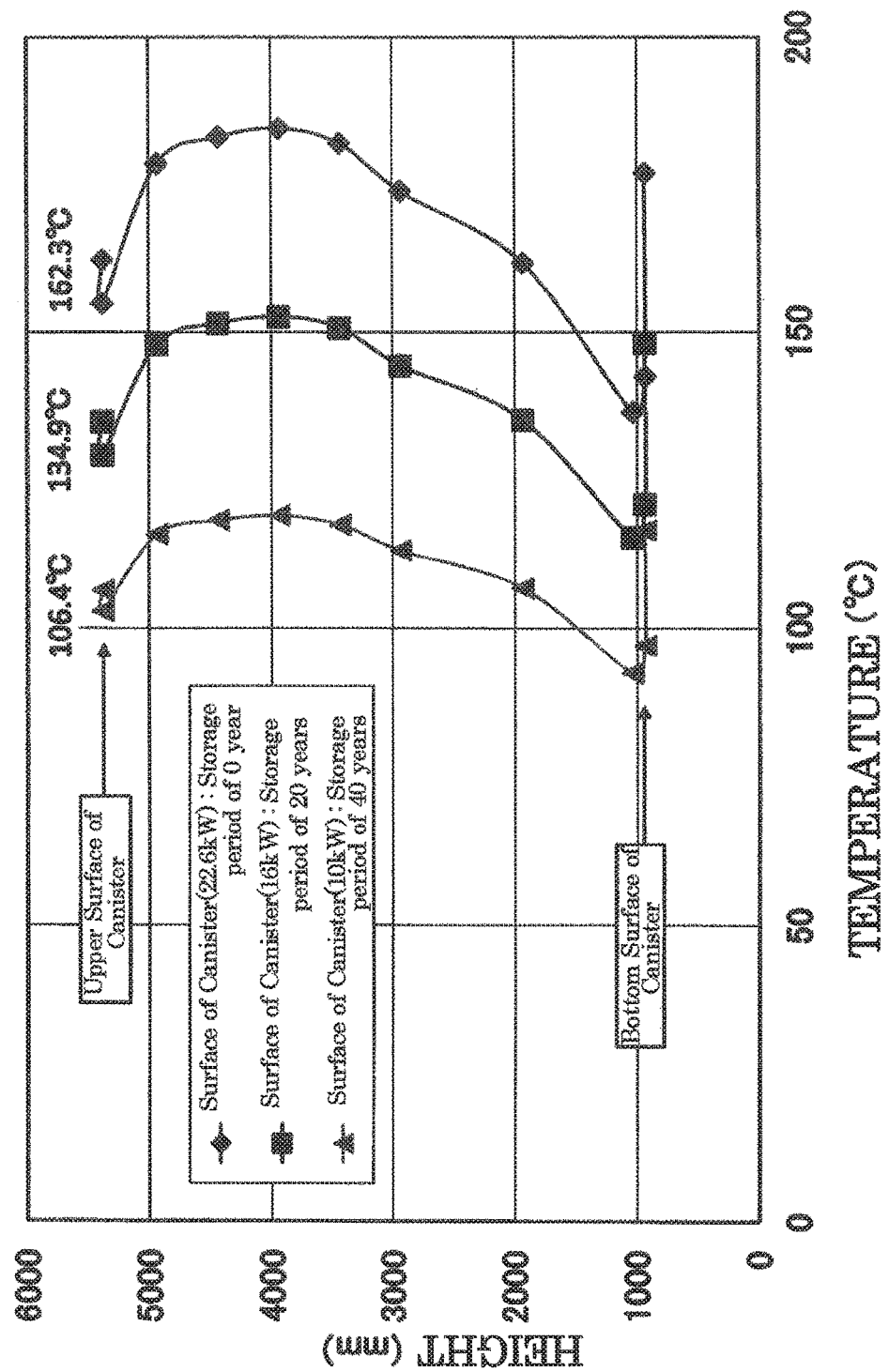
FIG. 35 is a graph illustrating an exemplary secular change of temperature distribution in a vertical direction of the canister in Case 1.

In the case where a storage period and a stored fuel kind are known, a heat generation amount, namely, an amount of decay heat can be calculated by using an analysis code. Therefore, a heat generation amount can be obtained by calculating the decay heat in accordance with the storage period. According to a heat removal experiment using a full-scale concrete cask model and performed simulating the above-described heat generation amount with a heater, for example, the canister top portion temperature $T_T$ in a CFS cask (Case 1) is 162.3° C. when the storage period is zero years, 134.9° C. when the storage period is 20 years, and 106.4° C. the storage period is 40 years as illustrated in FIG. 35. According to this, the canister top portion temperature $T_T$ decreases at a rate of 1.37° C. per year until 20 years and at a rate of 1.425° C. per year until 40 years.

In other words, when a kind of stored fuel is known, the heat generation amount can be obtained by calculating the decay heat in accordance with the storage period. Furthermore, an estimation value of the decreased temperature $T_d$ with age in accordance with the years of storage can be calculated by proportional calculation with a calculated heat generation amount and the test data corresponding to the concrete cask type of a monitoring target.

As for the maximum decreased temperature $T_{Ld}$ at the time of gas leakage, when a gas leakage test using a full-scale cask model is performed for each of the concrete casks of Cases 1 to 3 relative to zero years of storage (22.6 kW), an estimation value of the maximum decreased temperature $T_{Ld}$ at the time of gas leakage in accordance with the years of storage can be calculated by the proportional calculation. For example, in the case of the CFS cask having pressure decrease of 0.5 atm (Case 1), the maximum decreased temperature $T_{Ld}$ at the time of gas leakage is 6° C. when the storage period is zero years (22.6 kW). Therefore, since the years of storage, namely, the heat generation amount and canister temperature distribution are similar, in the case of executing proportional calculation, the estimation value becomes 5.4° C. when the storage period is 20 years (16 kW) and becomes 4.2° C. when the storage period is 40 (10 kW).

Additionally, the threshold temperature Ts is determined considering balance between, for example, the maximum decreased temperature $T_{Ld}$ at the time of gas leakage and determination of an error range based on data accumulation by monitoring during the proper operation time without occurrence of gas leakage. Simultaneously, the threshold temperature Ts is a physical amount, in other words, a physical quantity/a physical value, influenced by an installation position because a temperature value to be detected is varied by how close to the canister top portion $1_T$ the first temperature sensor 21 or 22 can be installed.

In the case where the first temperature sensor 21 can be set closest to the canister top portion $1_T$ like the bar-shaped thermometer illustrated in FIG. 2, the threshold temperature Ts may be calculated by following arithmetic processing: [threshold temperature Ts=(maximum decreased temperature $T_{Ld}$ at the time of gas leakage)/2]. Needless to mention, the maximum decreased temperature $T_{Ld}$ at the time of gas leakage becomes a little low because the lid bottom portion temperature $T_{LB}$ is measured at a position distant from the canister top portion $1_T$, and influence of the decreased temperature $T_d$ with age cannot be ignored. Therefore, preferably, the threshold temperature Ts is calculated as: [threshold temperature Ts=(maximum decreased temperature $T_{Ld}$ at the time of gas leakage−decreased temperature $T_d$ with age)/2].

Figure 32:
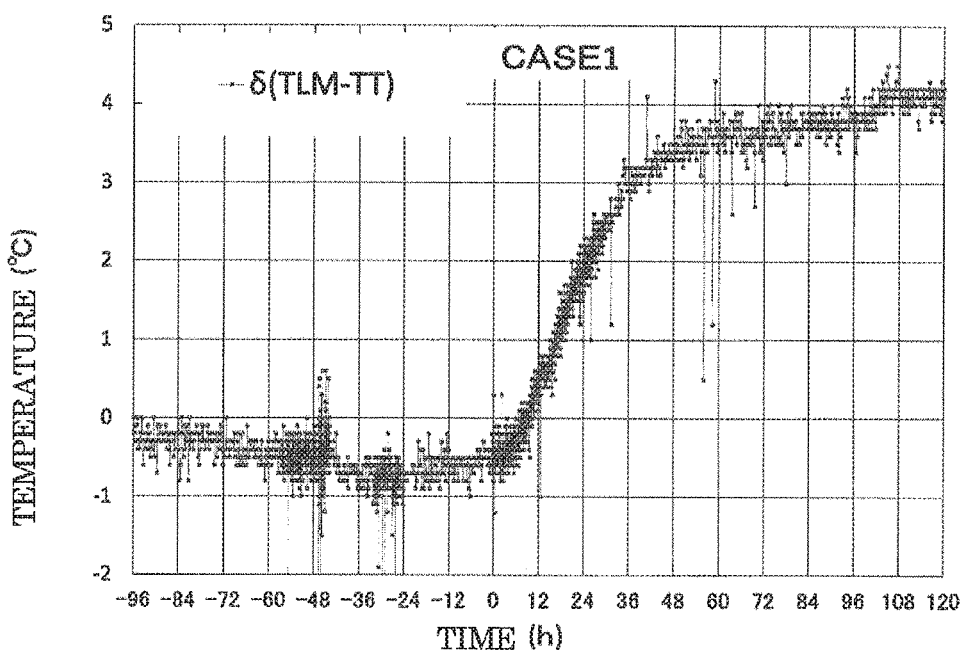
FIG. 32 is a graph illustrating an exemplary time variation of the difference $\delta(T_{LM}-T_{LB})$ from a reference temperature of the temperature difference $(T_{LM}-T_{LB})$ between the lid bottom portion temperature $T_{LB}$ and the lid inner temperature $T_{LM}$ before and after helium leakage in Case 1.

For example, in the case of the CFS cask in Case 1 in which the maximum decreased temperature $T_{Ld}$ at the time of gas leakage is 6° C. and the decreased temperature $T_d$ with age is about 1° C. per year, according to an example of FIG. 32 in which the first temperature sensor 21 is set closest to the canister top portion $1_T$, about 3 to 4° C. may be considered to be an appropriate setting value. According to an example of FIG. 34 in which the temperature $T_{LB}$ of the member that receives influence of the canister top portion temperature $T_T$ and is separated from the canister top portion $1_T$ is measured, about 2 to 3° C. may be considered to be an appropriate setting value. Meanwhile, it is appropriate to set the decreased temperature $T_d$ with age to 1° C. and set a data review period $t_0$ to one year.

Furthermore, the maximum decreased temperature $T_{Ld}$ at the time of gas leakage is largely influenced by change of inner pressure according to the gas leakage tests executed by the inventor. Additionally, since the amounts of decay heat is reduced in the maximum decreased temperature $T_{Ld}$ at the time of gas leakage and the decreased temperature $T_d$ with age with passage of the storage period, the temperatures tend to decrease even without occurrence of helium leakage.

In other words, since the maximum decreased temperature $T_{Ld}$ at the time of gas leakage is varied by change of the inner pressure and the amount of decay heat, it is not preferable to fix the threshold temperature Ts depending on circumstances. Therefore, preferably, the data review period $t_0$ is set, and the decreased temperature $T_d$ with age at the canister top portion is reviewed and the threshold temperature Ts to determine gas leakage is recalculated and determined every time the review period $t_0$ elapses.

Meanwhile, there is published data related to transition of temperature distribution of the respective portion and the like from beginning of storage to end of storage in a cask made of RC or a cask made of CFS. Therefore, the decreased temperature $T_d$ with age that may occur during the data review period $t_0$ can be easily determined based on such published heat removal test results in the casks.

Figure 30:
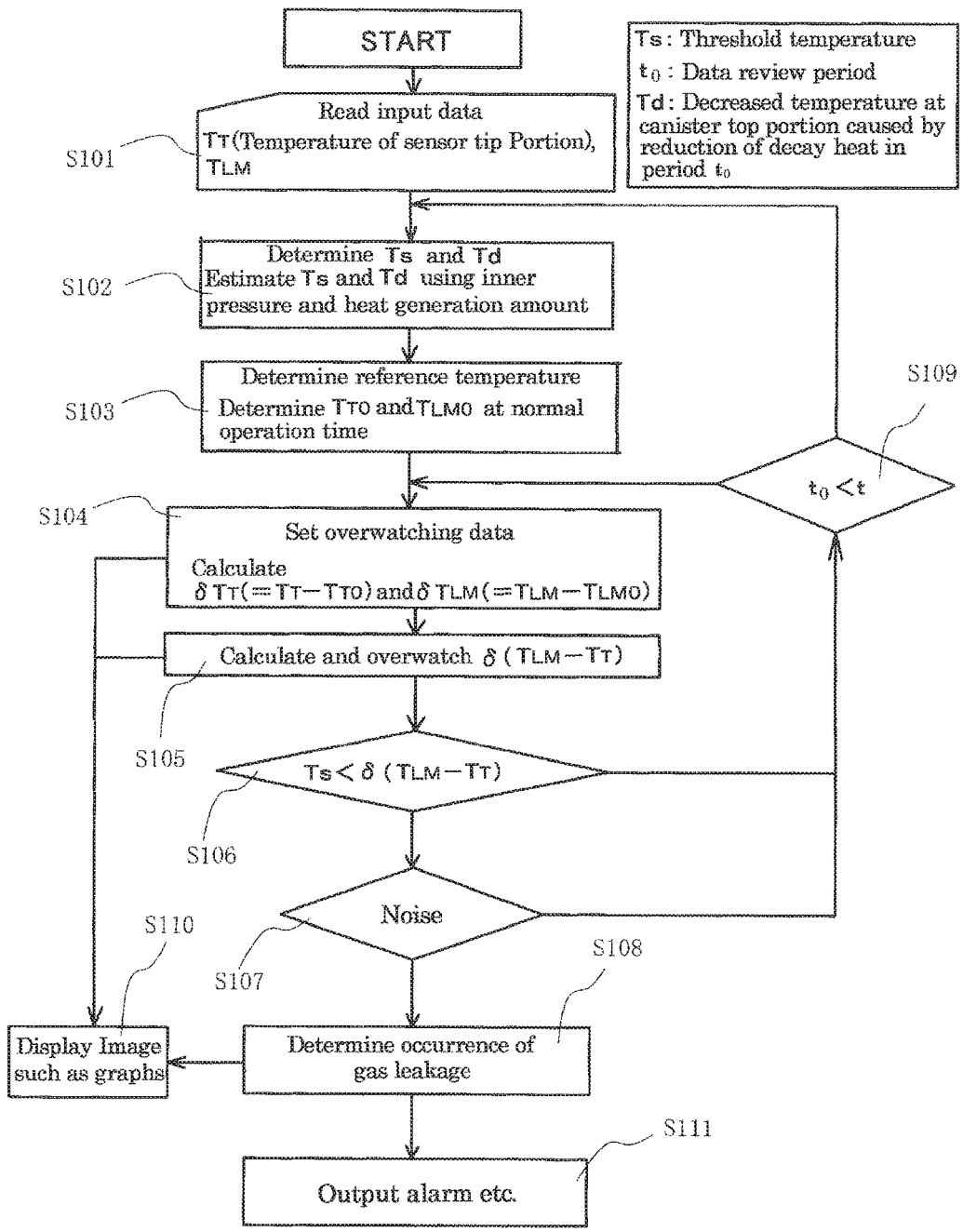
FIG. 30 is a flowchart illustrating an embodiment of an apparatus and a method for detecting gas leakage from a radioactive material sealed container according to the present invention.

In the following, a processing procedure in the apparatus for detecting gas leakage according to the present embodiment will be described based on a flowchart illustrated in FIG. 30.

First, the canister top portion temperature $T_T$ and the lid inner temperature $T_{LM}$ detected by the first and second temperature sensors 21, 17 are read from the temperature measurement device 26 (Step 101).

Next, the threshold temperature Ts to determine occurrence of gas leakage is calculated (Step 102). In the present embodiment, the threshold temperature Ts is suitably determined within a range from the maximum decreased temperature $T_{Ld}$ at the time of gas leakage or less and the decreased temperature $T_d$ with age or more after acquiring the maximum decreased temperature $T_{Ld}$ at the time of gas leakage and the decreased temperature $T_d$ with age at the canister top portion which are observed during the data review period $t_0$. For example, the threshold temperature Ts is calculated by Expression 1 or Expression 2 as shown below.

$$Ts = T_{Ld}/2 \quad \text{[Expression 1]}$$

$$Ts = (T_{Ld} - T_d)/2 \quad \text{[Expression 2]}$$

As just an example of the threshold temperature Ts, specifically, a value such as 3° C. or 2.5° C. is calculated in the case of the CFS cask in Case 1. Since the maximum decreased temperature $T_{Ld}$ at the time of gas leakage and the decreased temperature $T_d$ with age at the canister top portion are varied by the inner pressure of the canister and the heat generation amount, these temperatures are estimated from the data review period $t_0$ and knowledge achieved by calculation and past tests.

The data review period $t_0$ is not limited to a specific period, and suitably set considering magnitude of change assumed for the maximum decreased temperature $T_{Ld}$ at the time of gas leakage and the decreased temperature $T_d$ with age. As just an example of the data review period $t_0$, specifically, one year or two years may be exemplified.

Next, a reference temperature is determined. The reference temperature is an average value of each of the two temperatures $T_T$ and $T_{LM}$ during a period reference temperature without occurrence of helium leakage or a temperature at a certain time point during the proper operation time (Step 103).

The temperatures such as the canister top portion temperature $T_T$ and the lid inner temperature $T_{LM}$ are considered to keep a constant temperature difference and fluctuate in a long cycle unless otherwise gas leakage occurs. Therefore, an appropriate time during monitoring is determined, and each of temperatures at this time may be determined as a reference point. The time is optional, and in the present embodiment, for example, a value of −96 hours is adopted, but the time does not mean anything special.

The differences between the reference temperatures $T_{T0}$ and $T_{LM0}$ and the respective measured temperatures $T_T$ and $T_{LM}$, namely, the change amounts of the respective measured temperatures $\delta T_T$ and $\delta T_{LM}$ are calculated and set as monitoring data (Step 104).

Additionally, a difference $\delta(T_{LM}-T_T)$ between the temperature change amounts $\delta T_T$ and $\delta T_{LM}$ from the respective reference temperatures $T_{T0}$ and $T_{LM0}$ is calculated and monitored (Step 105).

Next, as quantitative determination, whether $Ts < \delta(T_{LM}-T_T)$ is satisfied is constantly monitored (Step 106). In the case where the above relation is satisfied, whether such a relation is a temporary phenomenon like noise is checked (Step 107).

Whether noise or not is determined by, for example, whether there is a predetermined temperature difference compared to previous and former data in the case where noticeable data is observed. Specifically, when there is the predetermined temperature difference, it is determined as noise. Since noise can be removed also by changing a sampling time, Step 107 is not needed in this case.

Figure 31:
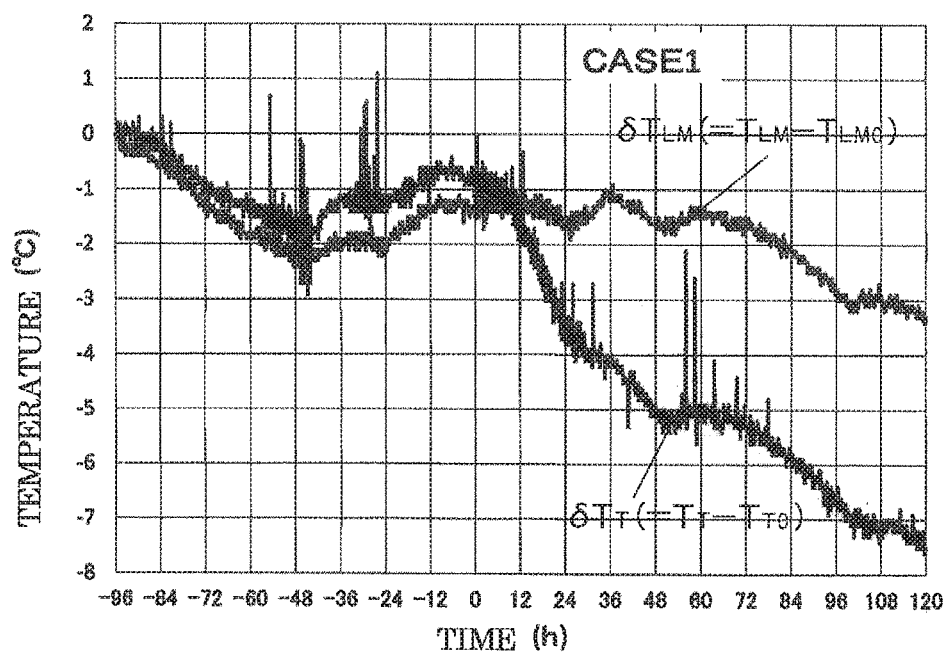
FIG. 31 is a graph illustrating an exemplary relation of time variations of differences of the canister top portion center temperature $T_T$ and the lid inner temperature $T_{LM}$ from reference temperatures before and after helium leakage in Case 1.
Figure 33:
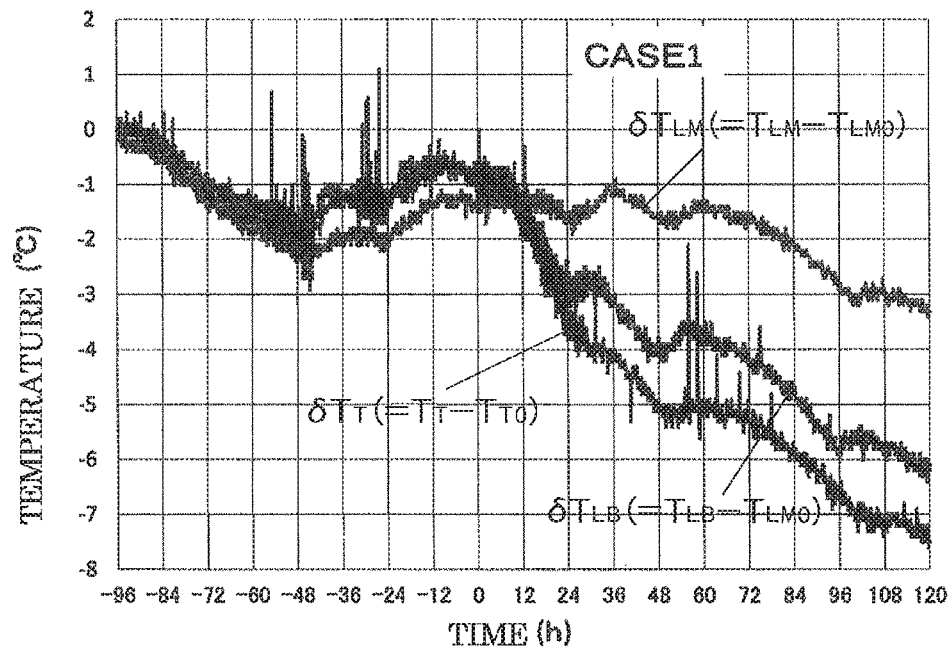
FIG. 33 is a graph illustrating an exemplary relation of time variations of differences of the lid inner temperature $T_{LM}$, the lid bottom portion temperature $T_{LB}$, and the canister top portion center temperature $T_T$ from reference temperatures before and after helium leakage in an embodiment in which a temperature of a temperature sensor set closest to the canister top portion is substituted as the canister top portion center temperature $T_T$ and a temperature of a metal plate on a bottom surface of the concrete lid is indicated as the lid bottom portion temperature $T_{LB}$ in Case 1.

Furthermore, in monitoring by the display device 35, the noticeable data shaped like a whisker as illustrated in the graphs of FIG. 31 or 33 can be easily determined as noise. when not determined as noise, it is determined as leakage (Step 108).

In this case, a warning sound, a warning message, and the like are output to the warning device 36 or the display device 35 (Steps 110 and 111).

On the other hand, in the case where $Ts < \delta(T_{LM}-T_T)$ is not satisfied or in the case where data is determined as noise although the relation is satisfied, whether a monitoring period t is longer than the data review period $t_0$ is checked (Step 109).

In the case where the monitoring period t is shorter than data review period $t_0$, it is determined as "No Abnormality", and the process returns to the processing in Step 104 and monitoring is continued.

On the other hand, in the case where the monitoring period t is longer than the data review period $t_0$, the process returns to the processing in Step 102, and the setting values (Ts, Td) are reviewed again (Step 102). Then, the reference values of the respective temperatures ($T_{T0}$, $T_{LM0}$) are reviewed (Step 103), and monitoring is continued (Step 104).

In other words, after the data review period $t_0$ passes, the decreased temperature $T_d$ with age at the canister top portion is estimated in accordance with years of storage by using the decay heat analysis results and test results, and the threshold temperature Ts to determine occurrence of gas leakage based on the decreased temperature $T_d$ with age is calculated and newly set (Step 102).

Meanwhile, as a gas leakage detection system, leakage may be determined by whether the temperature difference to be monitored by a computer is significant fluctuation or not. When the condition is satisfied, only an alarm may be issued, but as a safe measure as the detection system, real time monitoring for temperature in time-series is preferably provided in terms of confirming no abnormality.

Needless to mention, determination on presence of gas leakage can be easily made by a worker even without using the computer 30 if only the temperature changes of the lid inner temperature $T_{LM}$ and the canister top portion temperature $T_T$ or change of the temperature difference between these temperatures are displayed on the display device 35.

In other words, as described above as the characteristics found by the inventor, in the event of helium leakage from the inside of the canister 1, change is generated in the difference between the canister top portion temperature $T_T$ or the lid bottom portion temperature $T_{LB}$ and the lid inner temperature $T_{LM}$, and the change tends to be enlarged.

Judging from this, only by comparatively displaying, on the display device 35, the temperature changes of the lid inner temperature $T_{LM}$ and the canister top portion temperature $T_T$ or the lid bottom portion temperature $T_{LB}$, a monitoring person can visually and intuitively determine that a phenomenon different from normal operation time is occurring, and can estimate helium leakage.

For example, it may be considered that differences between respective temperatures at the measurement time and the respective average temperatures of the two temperatures during a period deemed as proper operation time without occurrence of helium leakage or respective temperatures of the two temperatures at a specific time point during the proper operation time (referred to as the reference temperature) are respectively calculated as change amounts, and additionally, a difference between these change amounts is acquired and monitored. In this case, when the difference between the temperature change amounts tends to increase, it can be determined that leakage is occurring.

Furthermore, in the case of directly comparing actual measurement temperatures of the two temperatures $T_T$ and $T_{LM}$ or actual measurement temperatures of the temperatures $T_{LB}$ and $T_{LM}$, when the temperature difference between both temperatures tends to be reduced, it can be determined that leakage is occurring. Furthermore, in the case of displaying two actual measurement temperatures to be compared also, the two actual measurement temperatures are multiply displayed, making the respective comparing average values of the two actual measurement temperatures the same. Consequently, when a deviation state in a graph illustrating changes of temperatures of both temperatures tends to be enlarged, it can be determined that leakage is occurring.

Figure 14:
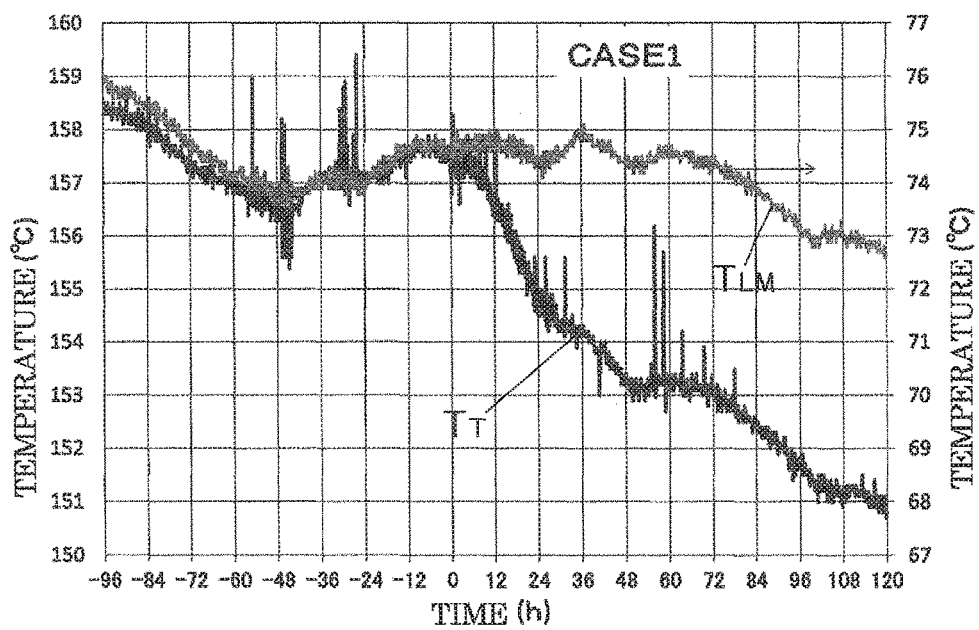
FIG. 14 is a graph illustrating a relation between the canister top portion center temperature $T_T$ and a concrete lid inner temperature $T_{LM}$ before and after helium leakage in Case 1.
Figure 17:
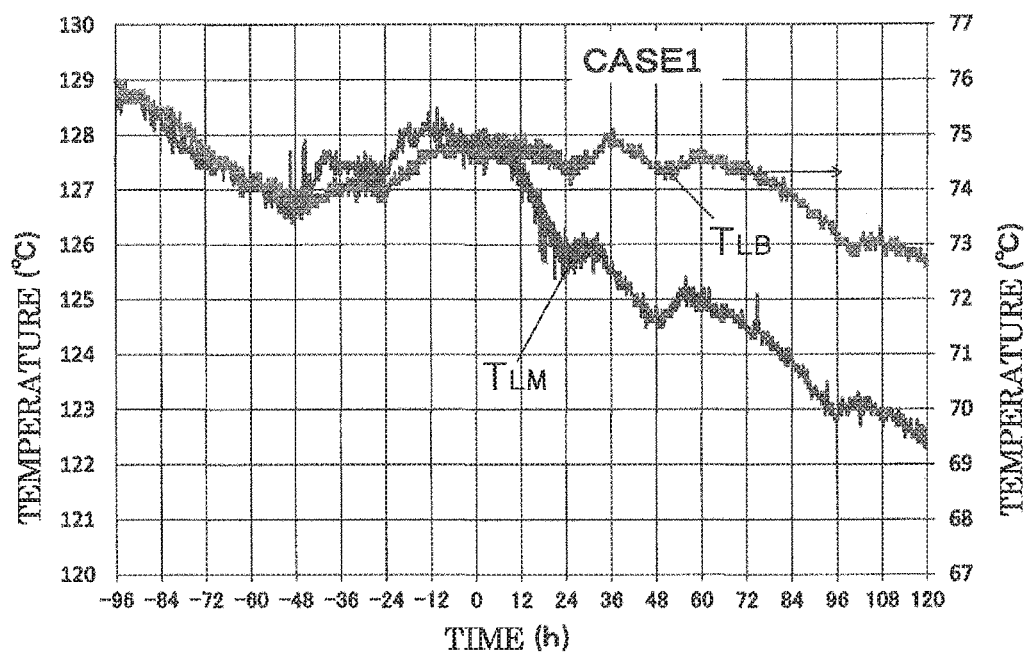
FIG. 17 is a graph illustrating a relation between the concrete lid bottom portion temperature $T_{LB}$ and the lid inner temperature $T_{LM}$ before and after helium leakage in Case 1.
Figure 18:
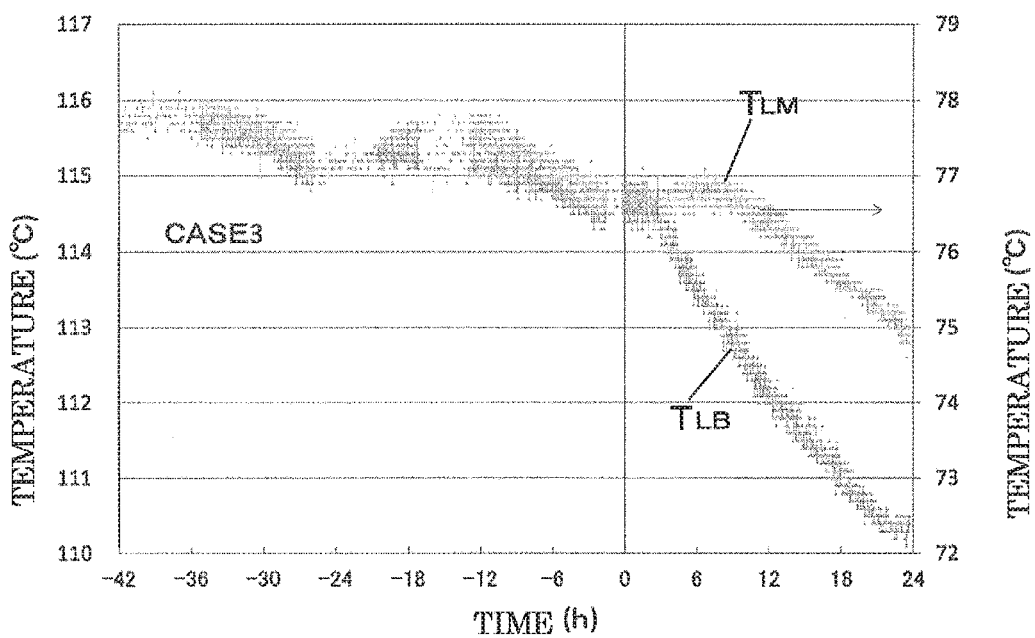
FIG. 18 is a graph illustrating a relation between the lid bottom portion temperature $T_{LB}$ and the lid inner temperature $T_{LM}$ before and after helium leakage in Case 3.

For example, as illustrated in FIGS. 14, 17, and 18, in the case of constantly displaying temperature change between the lid inner temperature $T_{LM}$ and the canister top portion temperature $T_T$ or the lid bottom portion temperature $T_{LB}$ (or $T_{LBI}$) on the display device in time series, the temperature change between the canister top portion temperature $T_T$ or the lid bottom portion temperature $T_{LB}$ (or $T_{LBI}$) and the lid inner temperature $T_{LM}$ can be monitored and compared. Therefore, in the case where deviation is generated in the graph of these temperatures and the deviation tends to be enlarged, namely, in the case where the difference between the two temperatures (relative difference) tends to be enlarged, it can be determined that helium leakage is occurring.

Figure 23:
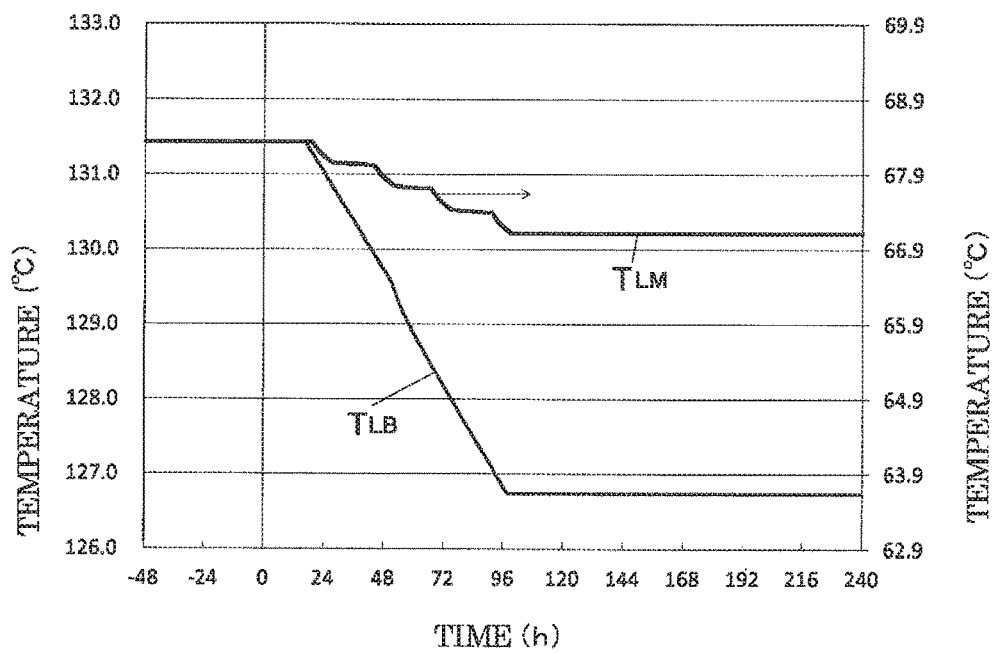
FIG. 23 is a graph illustrating a relation between the lid bottom portion temperature $T_{LB}$ and the lid inner temperature $T_{LM}$ before and after helium leakage in Case 1.
Figure 26:
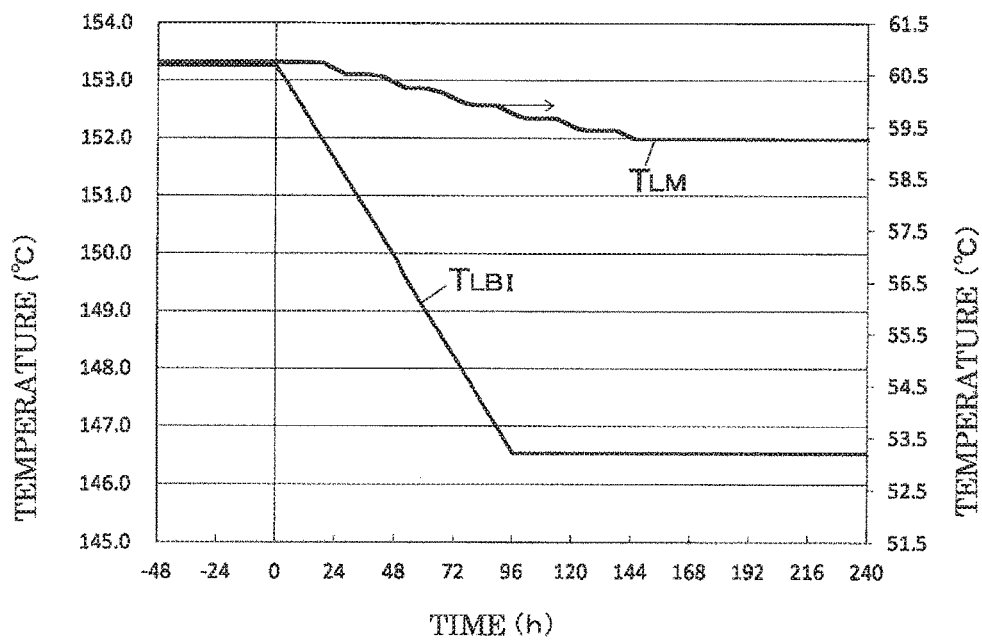
FIG. 26 is a graph illustrating a relation between the lid bottom portion temperature $T_{LB}$ and the lid inner temperature $T_{LM}$ before and after helium leakage when temperature sensors of Case 1 are arranged in a state as illustrated in FIG. 2.

Here, as illustrated in FIGS. 23 and 26, when display of the lid inner temperature $T_{LM}$ and the canister top portion temperature $T_T$ or display of the lid inner temperature $T_{LM}$ and the lid bottom portion temperature $T_{LB}$ are multiply displayed making the average values of the respective measurement amounts the same, it is possible to visually intuitively and easily grasp a tendency, as the deviation state of a plurality of graphs, in which a differences between the two temperatures (relative difference) is enlarged.

Furthermore, a display method of temperature data to be monitored on the display device 35 is not limited the above-described method. For example, preferably, presence of leakage can be estimated or can be determined by displaying, monitoring, and comparing, as illustrated in FIG. 31, the temperature change amounts $\delta T_{LM}$ and $\delta T_T$ from the respective reference temperatures at the canister top portion temperature $T_T$ and the lid inner temperature $T_{LM}$ in time series at the same time.

In this case, in the event of helium leakage, the deviation state generated between both temperatures changes can be more easily and visually grasped.

Furthermore, it may also be possible to read intermediate temperature data between the lid inner temperature $T_{LM}$ and the temperature at the tip of the bar-shaped thermometer set closest to the canister top portion, substituted as the canister top portion temperature $T_T$ (temperature of the first temperature sensor 21), such as the temperature $T_{LB}$ of the metal plate 14 of the concrete lid bottom portion, and monitor temperature differences ($\delta T_T$, $\delta T_{LB}$, $\delta T_{LM}$) between the respective reference temperatures and the respective temperatures ($T_T$, $T_{LB}$, $T_{LM}$) (refer to FIG. 33).

In this case, when helium leakage occurs from the inside of the canister 1, the deviation state in which obvious differences are generated between the temperatures at the three points, namely, a phenomenon in which time lag according to an influence level of the canister top portion temperature is generated in temperature change of the canister top portion temperature $T_T$ is significantly observed. Therefore, it is possible to easily and visually grasp the temperature change as a significant fluctuation.

Figure 24:
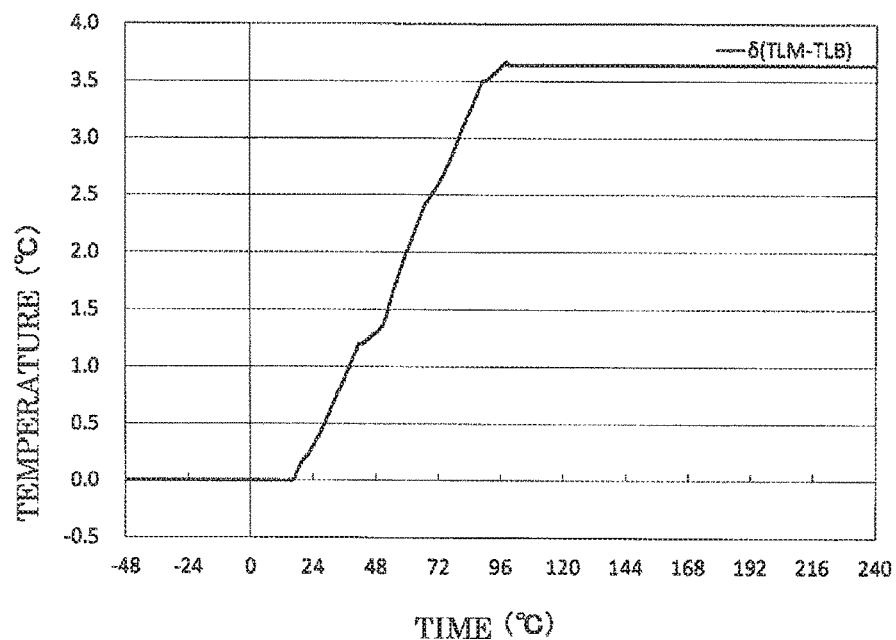
FIG. 24 is a graph illustrating a relation between a fluctuation difference $\delta(T_{LM}-T_{LB})$ between the lid bottom portion temperature $T_{LB}$ and the lid inner temperature $T_{LM}$ before and after helium leakage in Case 1.
Figure 27:
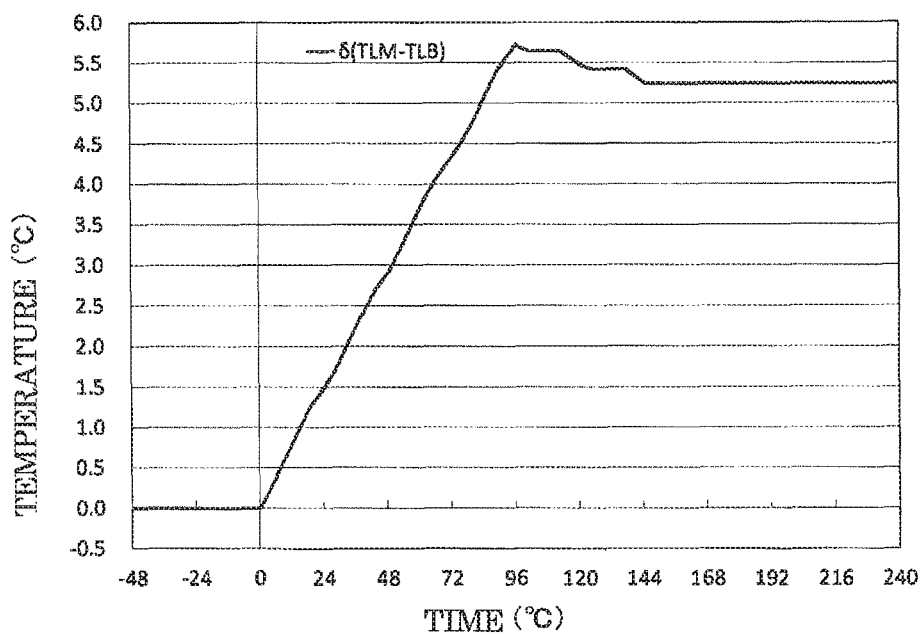
FIG. 27 is a graph illustrating a fluctuation difference $\delta(T_{LM}-T_{LB})$ between the lid bottom portion temperature $T_{LB}$ and the lid inner temperature $T_{LM}$ before and after helium leakage when temperature sensors of Case 1 are arranged in a state as illustrated in FIG. 2.

Additionally, for example, as illustrated in FIG. 24, 27, or 32, in the case of constantly displaying, on the display device 35, the difference of change amounts of the measured temperatures $\delta(T_{LM}-T_T)$ or $\delta(T_{LM}-T_{LB})$ between the lid inner temperature $T_{LM}$ and the canister top portion temperature $T_T$ or the lid bottom portion temperature $T_{LB}$ in time series, it is possible to easily and visually grasp occurrence of leakage because the value of $\delta(T_{LM}-T_{LB})$ shows rising movement when helium leakage occurs from the inside of the canister 1.

Figure 25:
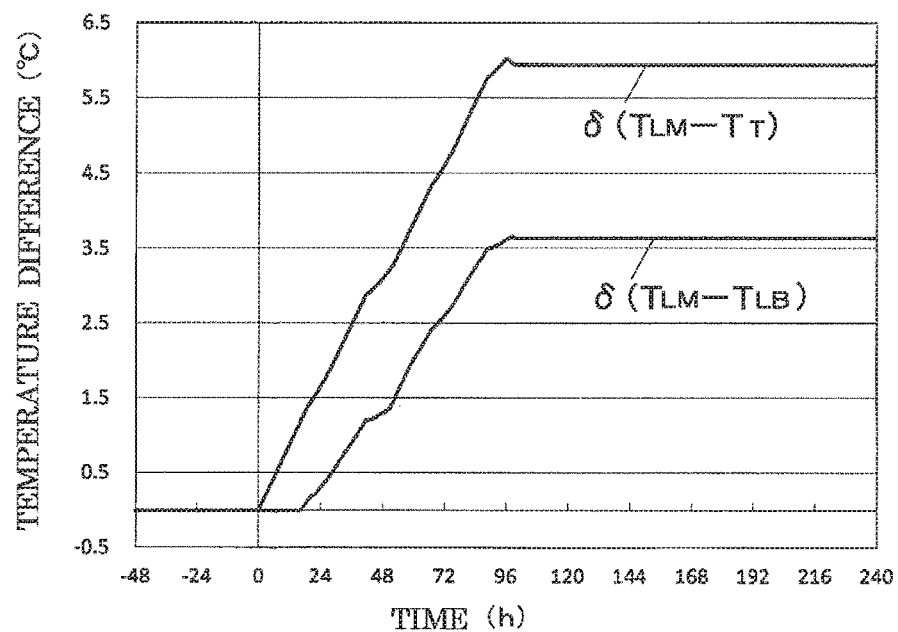
FIG. 25 is a graph illustrating fluctuation differences $\delta(T_{LM}-T_T)$ and $\delta(T_{LM}-T_{LB})$ between the lid bottom portion temperature $T_{LB}$, the canister top portion center temperature $T_T$, and the lid inner temperature $T_{LM}$ before and after helium leakage in Case 1.
Figure 28:
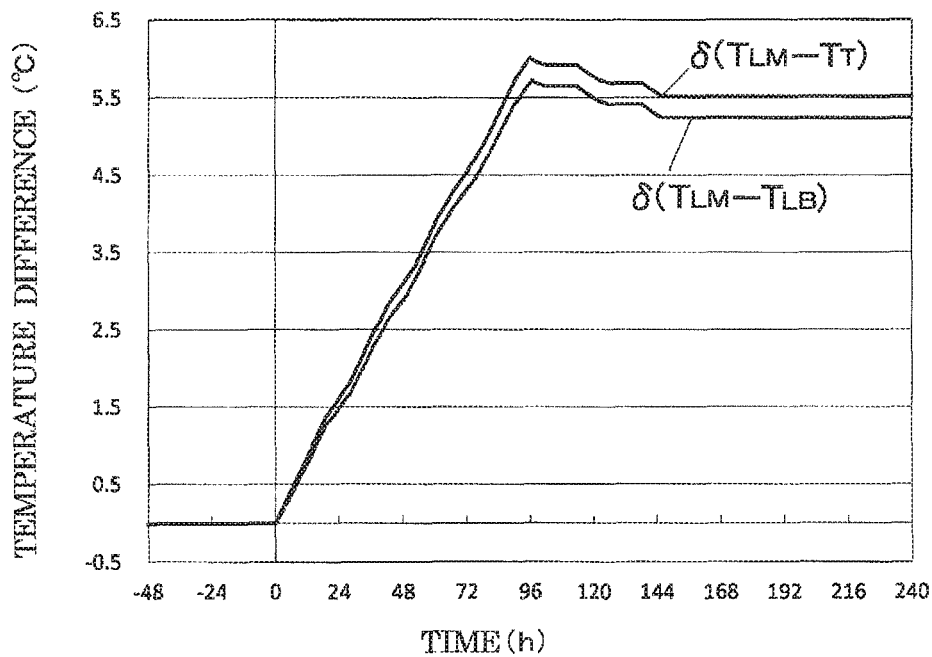
FIG. 28 is a graph illustrating fluctuation differences $\delta(T_{LM}-T_T)$ and $\delta(T_{LM}-T_{LB})$ between the lid bottom portion temperature $T_{LB}$, canister top portion center temperature $T_T$, and lid inner temperature $T_{LM}$ before and after helium leakage when temperature sensors of Case 1 are arranged in a state as illustrated in FIG. 2.
Figure 34:
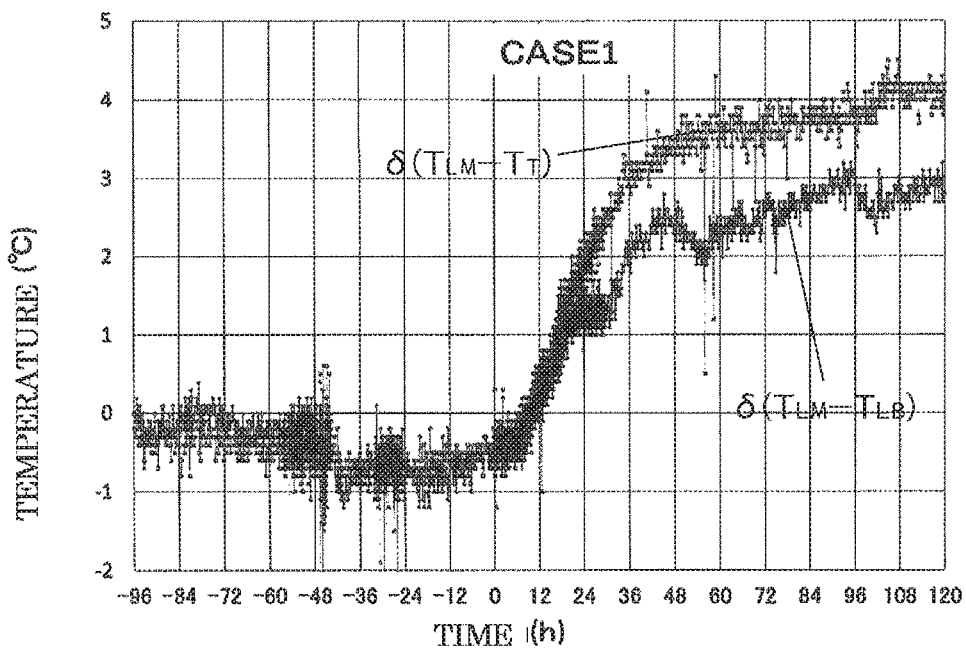
FIG. 34 is a graph illustrating an exemplary time variation of differences from reference temperatures of the temperature difference $(T_{LM}-T_{LB})$ between the lid inner temperature $T_{LM}$ and the lid bottom portion temperature $T_{LB}$, and the temperature difference $(T_{LM}-T_T)$ between the lid inner temperature $T_{LM}$ and the canister top portion center temperature $T_T$ before and after helium leakage in the embodiment in which the temperature of the temperature sensor set closest to the canister top portion is substituted as the canister top portion center temperature $T_T$ and the temperature of the metal plate on the bottom surface of the concrete lid is indicated as the lid bottom portion temperature $T_{LB}$ in Case 1.

Furthermore, as illustrated in FIGS. 25, 28, and 34, in the case of displaying, on the display device 35, the differences of the temperature change amounts $\delta(T_{LM}-T_T)$ and $\delta(T_{LM}-T_{LB})$ between the lid inner temperature $T_{LM}$ and the canister top portion temperature $T_T$ and between the lid inner temperature $T_{LM}$ and the lid bottom portion temperature $T_{LB}$ from the respective reference temperatures in time series, it is possible to easily and visually grasp occurrence of leakage because the values of $\delta(T_{LM}-T_T)$ and $\delta(T_{LM}-T_{LB})$ show rising movement with time lag when helium leakage occurs. Both $(T_{LM}-T_T)$ and $\delta(T_{LM}-T_{LB})$ start rising from zero hours after start of helium leakage, and temperature movement in which a temperature difference between both temperature is generated can be monitored in 24 hours. Therefore, it is possible to visually and intuitively determine that a phenomenon obviously different from normal operation time is occurring (temperature difference is having significant fluctuation).

Normally, as illustrated in FIG. 31 or 33, time variation (time variation of differences) of the temperature change amounts $\delta T_{LM}$, $\delta T_T$, and/or $\delta T_{LB}$ from the respective reference temperatures of the above-described lid inner temperature $T_{LM}$ and canister top portion temperature $T_T$ and/or lid bottom portion temperature $T_{LB}$ are displayed and compared on the display device 35, and is made available for monitoring as an item of daily inspection work of a worker. When a difference is observed between the respective temperature change amounts in such monitoring, a screen display is switched to the display in FIG. 32 or 34 and an amount of the difference is confirmed.

Meanwhile, displaying measured temperature change is a function which can be implemented by using a monitor of an existing data logger without relying on particular arithmetic processing by a computer, and also such a display can be easily achieved by installing software bundled with the data logger in a personal computer. Additionally, switching screen display is a general function which can be easily executed by using a commercially available data logger monitor or by the software bundled to the data logger and installed in the personal computer.

Meanwhile, the above-described embodiment is an example of preferable implementation of the present invention, but the present invention is not limited thereto, and various modifications can be made within a scope without departing from the gist of the present invention.

For example, in the present embodiment, the description has been mainly provided for the example of inserting the bar-shaped thermometer 4 including the second temperature sensor 17 and the first temperature sensor 21 or 22 into the penetration hole 25 opened at the concrete lid 3, but not limited thereto, there may be another possible manufacture in which a thermocouple is preliminarily embedded inside the concrete 11 at the time of manufacturing the concrete lid 3 and a wire is preliminarily led to the outside after pasting the thermocouple on a front surface or a back surface facing the canister top portion of the metal plate 14 at the bottom portion. Needless to mention, a temperature may also be measured at a place close to the canister top portion $1_T$ by making a portion of the metal plate 14 of the bottom portion of the concrete lid 3 project to the vicinity of the canister top portion $1_T$.

In the following, a description will be provided for matters and results of experiments that support effectiveness of the method and apparatus for detecting gas leakage from radioactive material sealed container according to the present invention.

<Experiments>
(1) Helium Leakage Test Conditions

Helium leakage tests from a canister were performed using a full-scale concrete cask model. The cask structures used in the leakage tests are illustrated in FIGS. 4A, 4B, and 4C. Additionally, test conditions are described in Table 1.

TABLE 1

| CASE No. | Cask Structure | Inner Pressure Before Leakage (kPa) | Leakage Rate (Pa · m³/s) |
|---|---|---|---|
| CASE 1 | CFS | 56 | $4.86 \times 10^{-1}$ |
| CASE 2 | CFS (Lid having outlet ducts with low flow resistance) | 151 | 5.16 |
| CASE 3 | RC | 59 | $3.60 \times 10$ |

<Case 1>

An openable/closable valve (not illustrated) was provided at a canister 1 of a concrete cask having a CFS structure illustrated in FIG. 4A, an electric heater (not illustrated) simulating a nuclear reactor spent fuel rod was housed inside the canister 1 under the same conditions as an actual spent fuel rod, and helium was filled at an atmospheric level (0 kPa in gauge pressure). Thus, an initial storage state of spent nuclear fuel was simulated in the concrete cask (heat generation amount 22.6 kW).

Inner pressure of the canister 1 rose by heat generation of the electric heater, and a steady state was obtained at gauge pressure 56 kPa. After that, the canister top portion temperature $T_T$, canister bottom portion temperature $T_B$, feeding air temperature $T_{IN}$, lid bottom portion temperature $T_{LB}$, concrete lid upper portion temperature $T_{LT}$, lid inner temperature $T_{LM}$, and an air temperature $T_{LA}$ between the concrete lid bottom portion and the canister top portion were continuously measured by the thermocouple provided at each of seven measurement points illustrated in FIG. 4A.

Then, subsequently, helium was made to leak rapidly by loosening the valve provided at the canister 1, and pressure was reduced by 50 kPa in two days, and the inner pressure of the canister 1 was reduced to become nearly the atmospheric pressure level four days later. Meanwhile, an amount of decay heat was calculated by an analysis code.

<Case 2>

Additionally, helium was also filled same as above in a canister 1 of a concrete cask having a CFS structure using a lid having outlet ducts with low flow resistance illustrated in FIG. 4B, and inner pressure of the canister 1 was raised and a steady state was obtained at gauge pressure 151 kPa. Then, temperatures at seven measurement points illustrated in FIG. 4B were continuously measured in the same manner as Case 1.

The inner pressure of the canister 1 was reduced to a nearly atmospheric pressure level in about one day by rapidly leaking helium.

<Case 3>

Additionally, helium was also filled same as above in a canister 1 of a concrete cask having an RC structure having an air inlet port shaped differently from Cases 1 and 2 illustrated in FIG. 4C, and inner pressure of the canister 1 was raised and a steady state was obtained at gauge pressure 59 kPa. Then, temperatures at seven measurement points illustrated in FIG. 4C were continuously measured in the same manner as Case 1.

The inner pressure of the canister 1 was reduced by rapidly leaking helium so as to become nearly the atmospheric pressure level in about two to three hours.

(2) Helium Leakage Test Results

Temperature measurement results at the respective measurement points are illustrated in FIGS. 5 to 28.

(i) First, in FIGS. 5 to 10, a relation of the canister top portion temperature $T_T$ and the canister bottom portion temperature $T_B$ with the inner pressure inside canister 1 and a relation of the canister top portion temperature $T_T$ and canister bottom portion temperature $T_B$ with the feeding air temperature $T_{IN}$ in Cases 1 to 3 will be described. In all of Cases, the canister top portion temperature $T_T$ decreased and the canister bottom portion temperature $T_B$ rose immediately after helium leakage (zero seconds is leakage start time) (refer to FIGS. 5, 7, and 9).

Figure 6:
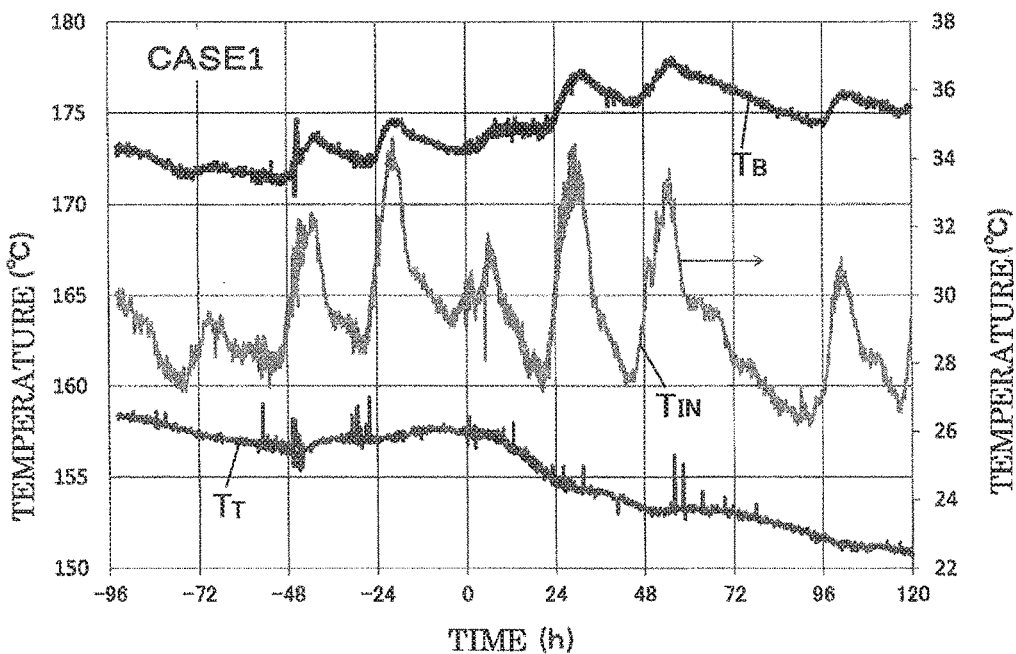
FIG. 6 is a graph illustrating a relation of the canister top portion center temperature $T_T$ and the canister bottom portion center temperature $T_B$ with a feeding air temperature $T_{IN}$ before and after helium leakage in Case 1.
Figure 7:
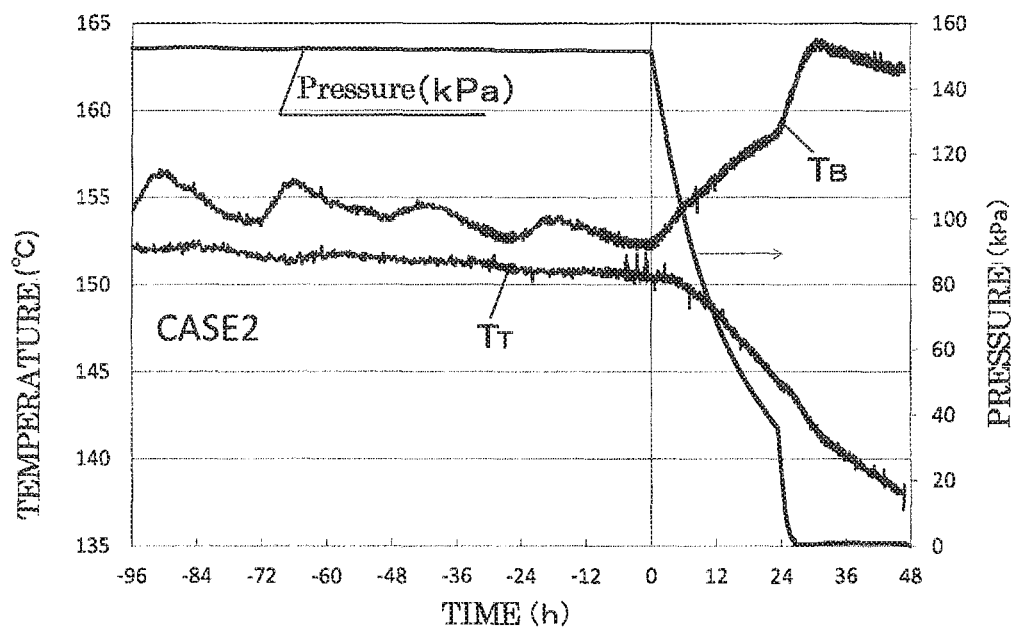
FIG. 7 is a graph illustrating change of a canister top portion center temperature $T_T$ and change of a canister bottom portion center temperature $T_B$ relative to inner pressure of a canister before and after helium leakage in Case 2.
Figure 8:
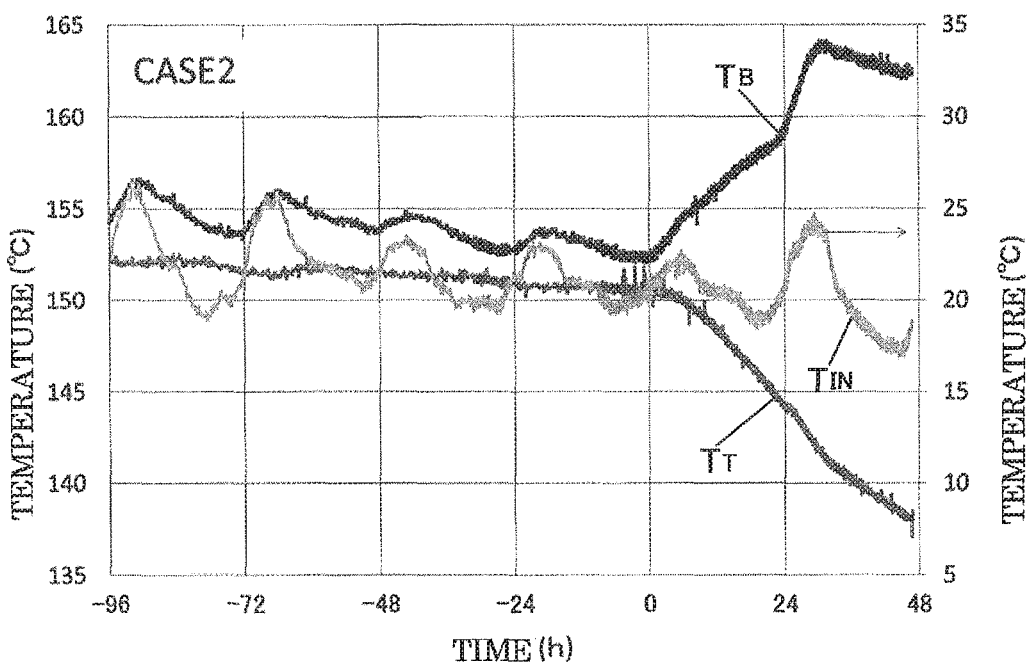
FIG. 8 is a graph illustrating a relation of the canister top portion center temperature $T_T$ and the canister bottom portion center temperature $T_B$ with an feeding air temperature $T_{IN}$ before and after helium leakage in Case 2.
Figure 9:
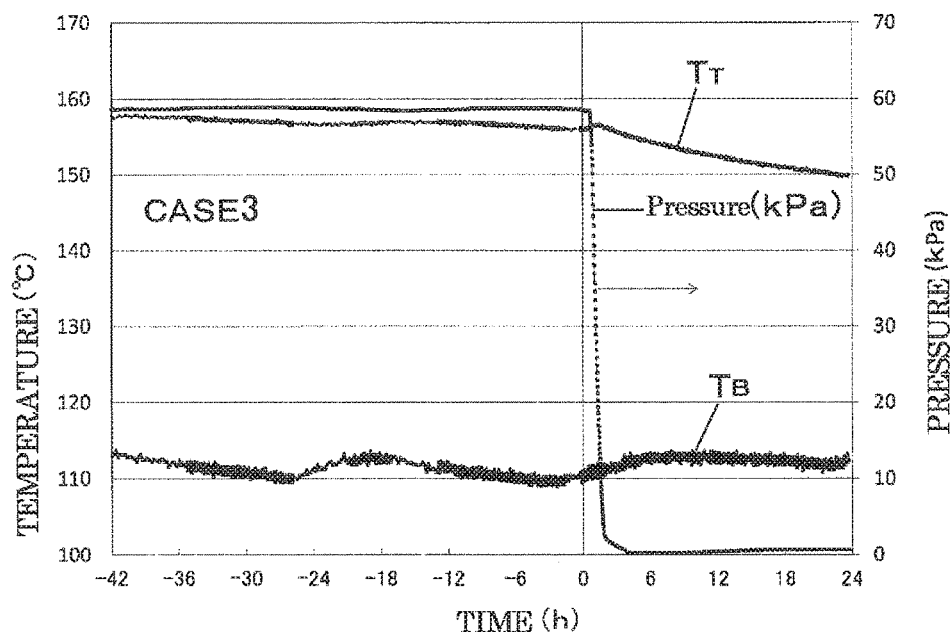
FIG. 9 is a graph illustrating change of a canister top portion center temperature $T_T$ and change of a canister bottom portion center temperature $T_B$ relative to inner pressure of a canister before and after helium leakage in Case 3.
Figure 10:
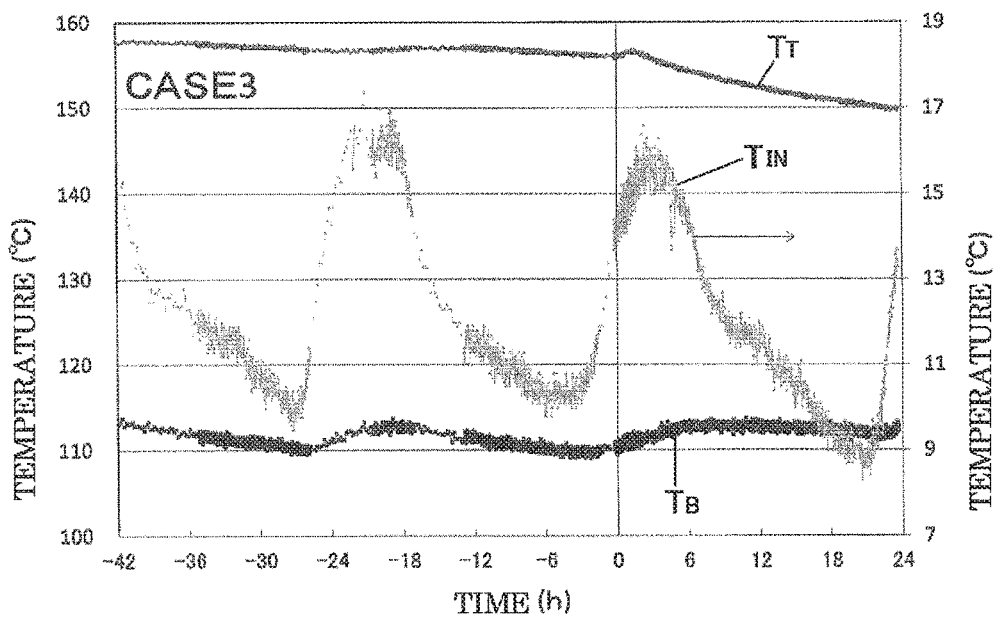
FIG. 10 is a graph illustrating a relation of the canister top portion center temperature $T_T$ and the canister bottom portion center temperature $T_B$ with an feeding air temperature $T_{IN}$ before and after helium leakage in Case 3.

Furthermore, it has been found that the bottom portion of the canister 1 was largely influenced by external air/cooling air flowing from the air inlet port 7, and the canister bottom portion temperature $T_B$ changed following daily fluctuation of the feeding air temperature $T_{IN}$ (refer to FIGS. 6, 8, and 10).

On the other hand, it has been found that the canister top portion $1_T$ in Cases 1 and 2 received influence of long-term temperature fluctuation of the external air 5 in about a five-day cycle but did not receive influence of daily fluctuation because a space between the concrete lid 3 and the canister 1 was narrow and high-temperature air stagnated (refer to FIGS. 6 and 8).

This implies that a temperature difference between the canister top portion temperature $T_T$ and the canister bottom portion temperature $T_B$ causes daily fluctuation by receiving influence of the feeding air temperature $T_{IN}$. Additionally, even in the case of having different structures of the concrete cask, to one degree or another, the same tendency was observed.

Meanwhile, in Case 2 in which the inner pressure of helium was made high, influence of helium leakage/pressure change given to the canister top portion temperature $T_T$ and the canister bottom portion temperature $T_B$ was large, and a significant gap of the temperature difference between the canister top portion temperature $T_T$ and the canister bottom portion temperature $T_B$ was observed.

(ii) On the other hand, FIGS. 11 to 16 illustrate a relation between change of the canister inner pressure and change of the canister top portion temperature $T_T$ and a relation between the canister top portion temperature $T_T$ and temperatures at other positions before and after helium leakage (zero seconds is leakage start time) in Case 1.

Figure 11:
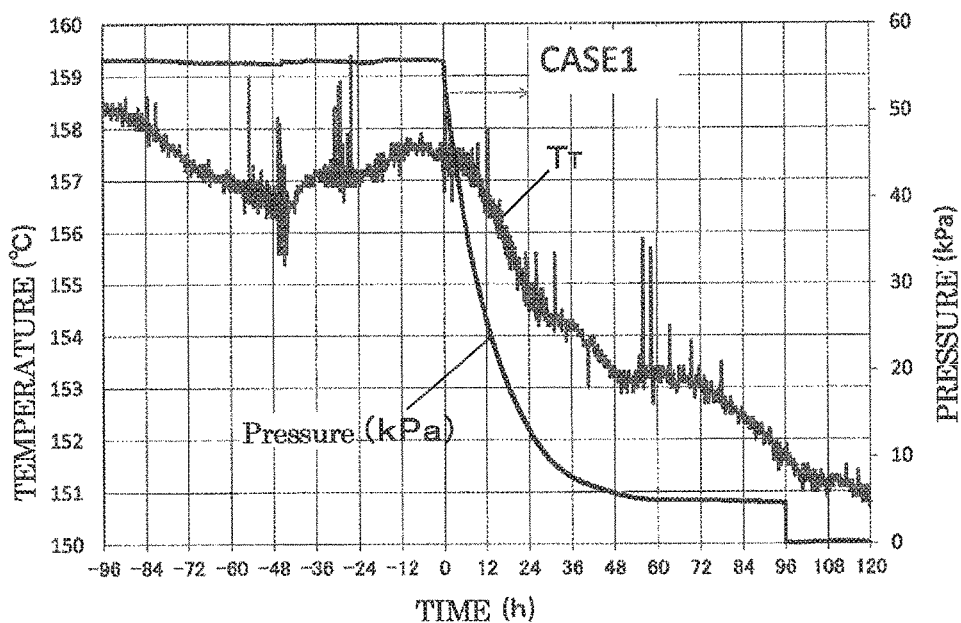
FIG. 11 is a graph illustrating change of the canister top portion center temperature $T_T$ relative to the inner pressure of the canister before and after helium leakage in Case 1.
Figure 12:
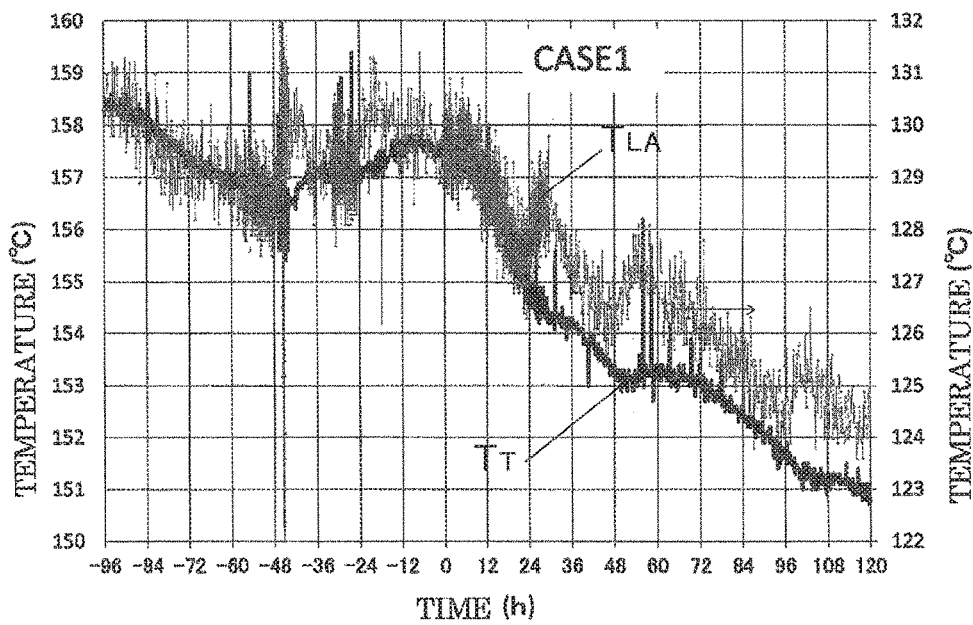
FIG. 12 is a graph illustrating a relation between the canister top portion center temperature $T_T$ and an air temperature $T_{LA}$ between a concrete lid bottom portion and the canister top portion before and after helium leakage in Case 1.

First, the relation between the canister top portion temperature $T_T$ and the inner pressure of the canister 1 has a relation in which both decrease immediately after helium leakage (refer to FIG. 11). Furthermore, the air temperature $T_{LA}$ between the concrete lid bottom portion and the canister top portion receives influence of temperature fluctuation of the external air (refer to FIG. 12).

Figure 15:
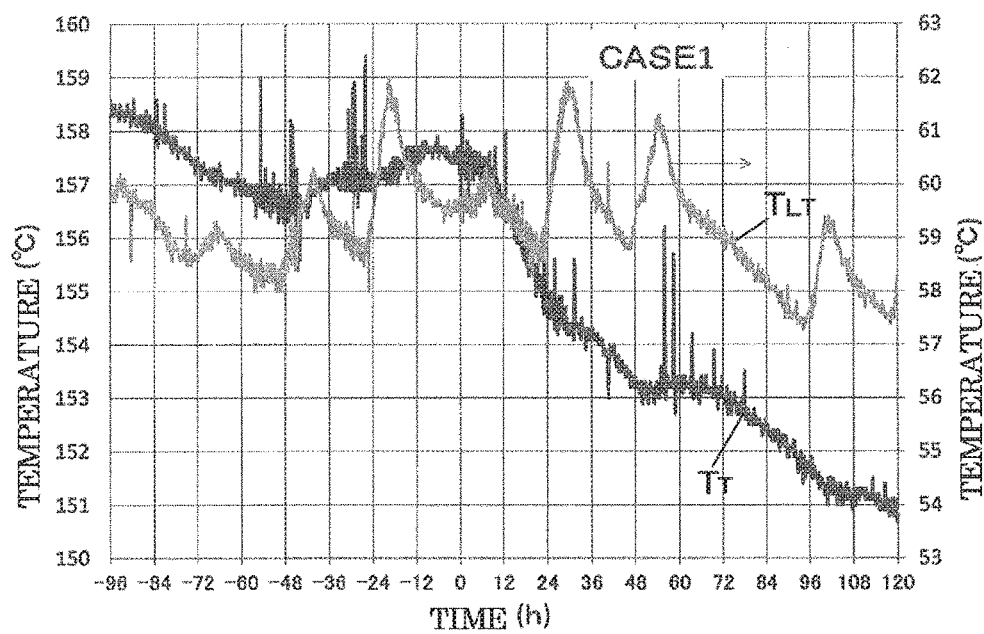
FIG. 15 is a graph illustrating a relation between the canister top portion center temperature $T_T$ and a concrete lid upper portion temperature $T_{LT}$ before and after helium leakage in Case 1.
Figure 16:
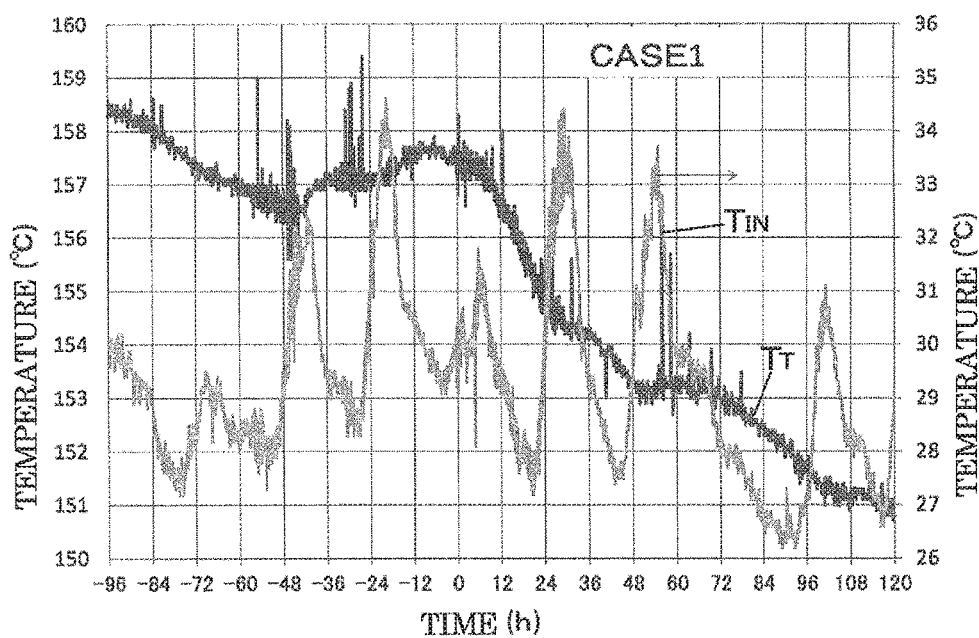
FIG. 16 is a graph illustrating a relation between the canister top portion center temperature $T_T$ and the feeding air temperature $T_{IN}$ before and after helium leakage in Case 1.

Furthermore, the canister top portion temperature $T_T$ receive neither influence of fluctuation of the feeding air temperature $T_{IN}$ (refer to FIG. 16) nor influence of temperature fluctuation of the concrete lid upper portion temperature $T_{LT}$ (refer to FIG. 15).

Figure 13:
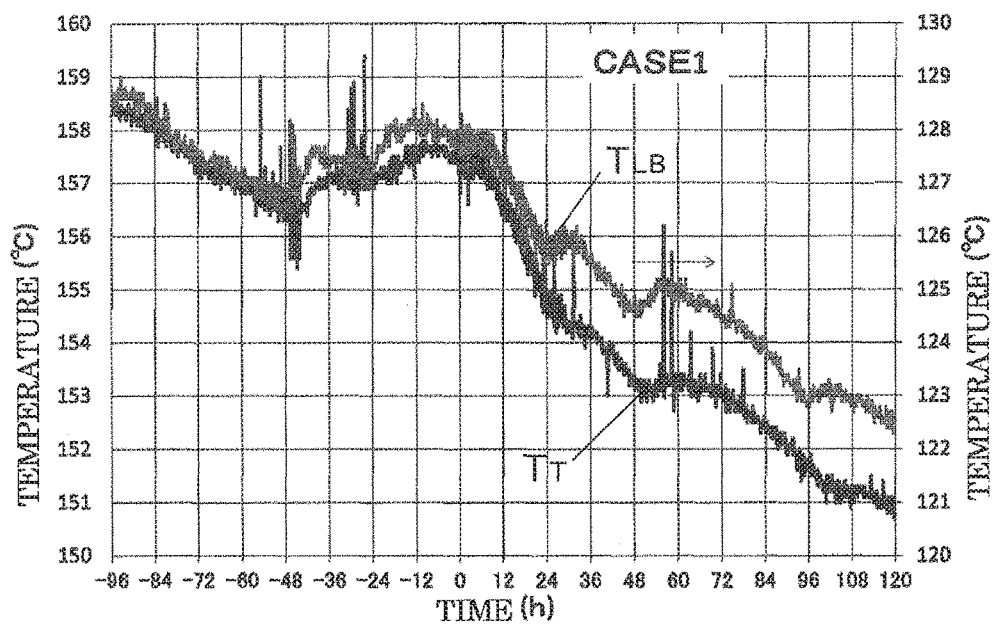
FIG. 13 is a graph illustrating a relation between the canister top portion center temperature $T_T$ and a concrete lid bottom portion temperature $T_{LB}$ relative to the inner pressure of the canister before and after helium leakage in Case 1.

Furthermore, it is obvious that the concrete lid upper portion temperature $T_{LT}$ receives influence of temperature fluctuation of the external air (refer to FIG. 15), and the lid inner temperature $T_{LM}$ and the lid bottom portion temperature $T_{LB}$ do not receive much influence of the external air (refer to FIGS. 14 and 13).

Additionally, it is found that the lid bottom portion temperature $T_{LB}$ sensitively follows the canister top portion temperature $T_T$ even after leakage has started although there is some time lag (refer to FIG. 13), and the lid inner temperature $T_{LM}$ insensitively follows the canister top portion temperature $T_T$ (refer to FIG. 14).

In other words, it is found that both the lid bottom portion temperature $T_{LB}$ and the lid inner temperature $T_{LM}$ each keep a constant temperature difference during normal operation time without occurrence of helium leakage, but in the event of helium leakage, the lid bottom portion temperature $T_{LB}$ decreases while the lid inner temperature $T_{LM}$ does not decrease. It is estimated that this is caused by the fact that the lid bottom portion temperature $T_{LB}$ follows the canister top portion temperature $T_T$ while the lid inner temperature $T_{LM}$ does not follow the canister top portion temperature $T_T$.

Meanwhile, in the present experiments, a temperature at the center of the canister top portion $1_T$ where temperature change is maximum is adopted as the canister top portion temperature $T_T$. Since the temperature change of the canister top portion temperature $T_T$ caused by helium leakage at the center portion thereof is maximum, this temperature change is optimal for detecting helium leakage, but not limited to the temperature change at the center portion, temperature change at a peripheral region distant from the center of the canister 1 and the concrete lid 3 may also be used depending on circumstances.

Based on the above experiments results, it is found that helium leakage information can be detected by comparing the temperature change between the lid bottom portion temperature $T_{LB}$ and the lid inner temperature $T_{LM}$. In other words, as illustrated in FIG. 17, a factor of increasing the temperature difference between both temperatures is estimated to be helium leakage from the canister 1. This tendency was also observed in Case 3 in which the cask having a different-shape flow passage as illustrated in FIG. 18.

In other words, it is found that it can be estimated that helium leaks from the canister by monitoring and comparing the lid bottom portion temperature $T_{LB}$ and the lid inner temperature $T_{LM}$ in the case where the temperature difference between both temperatures is increased (the temperature difference is significant fluctuation).

(3) Understanding Phenomenon Based on Analysis

Figure 3:
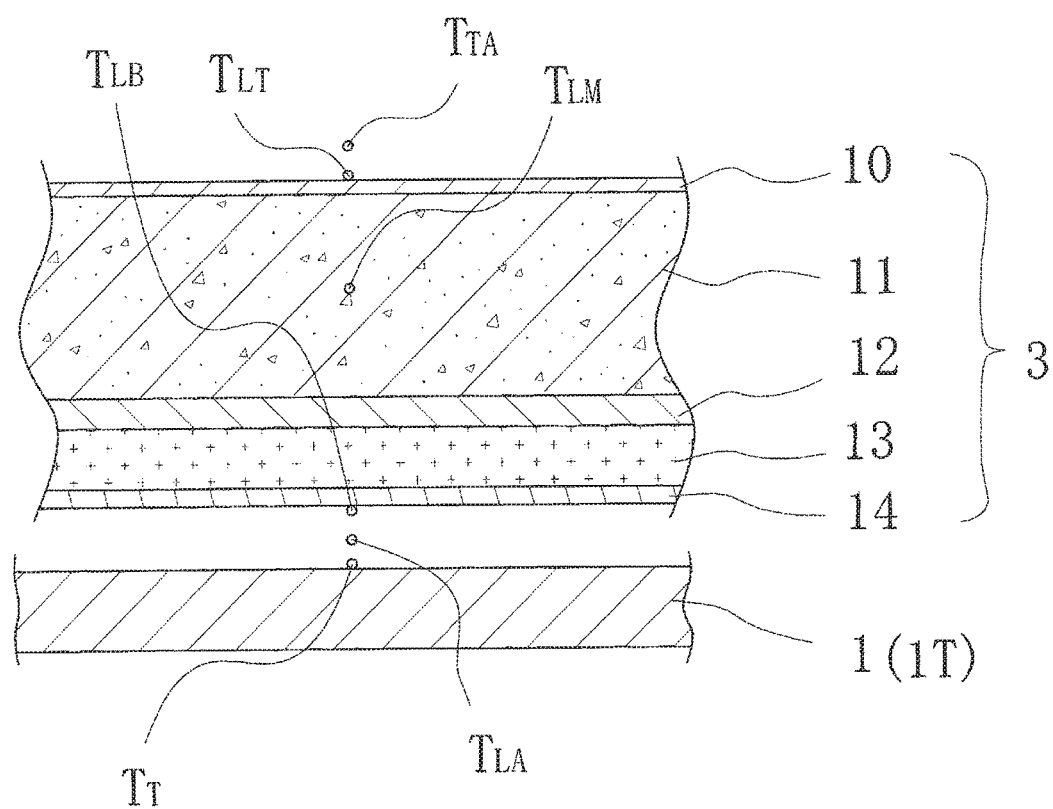
FIG. 3 is an explanatory diagram illustrating positions of temperature measurement points in an experiment supporting usability of the present invention.
Figure 19:
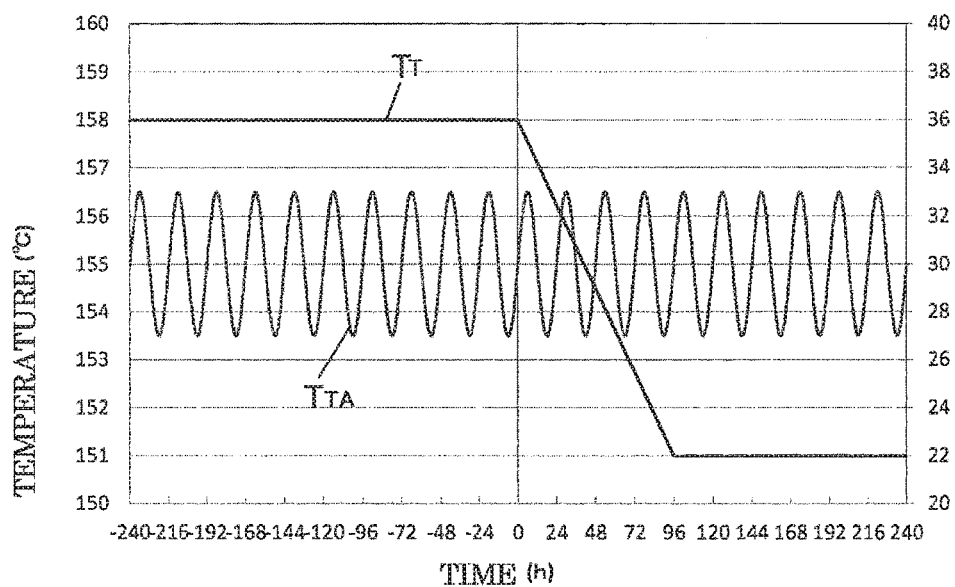
FIG. 19 is a graph illustrating a relation between daily fluctuation of the concrete lid upper portion air temperature $T_{TA}$ and change of the canister top portion center temperature $T_T$ before and after helium leakage in Case 1.

In order to study temperature change from the canister top portion $1_T$ to the concrete lid upper portion, non-constant one dimensional thermal conduction analysis was performed at the respective measurement points illustrated in FIG. 3. Meanwhile, as illustrated in FIG. 19, as for boundary conditions, the canister top portion temperature $T_T$ is set to linearly lower by 7° C. from 158° C. to 151° C. in 96 hours (four days) from leakage start (zero hours) while the concrete lid upper portion air temperature $T_{TA}$ is provided with a temperature condition that is daily fluctuation in a 24-hour cycle with a fluctuation width of ±3° C. at an average temperature 30° C.

Figure 20:
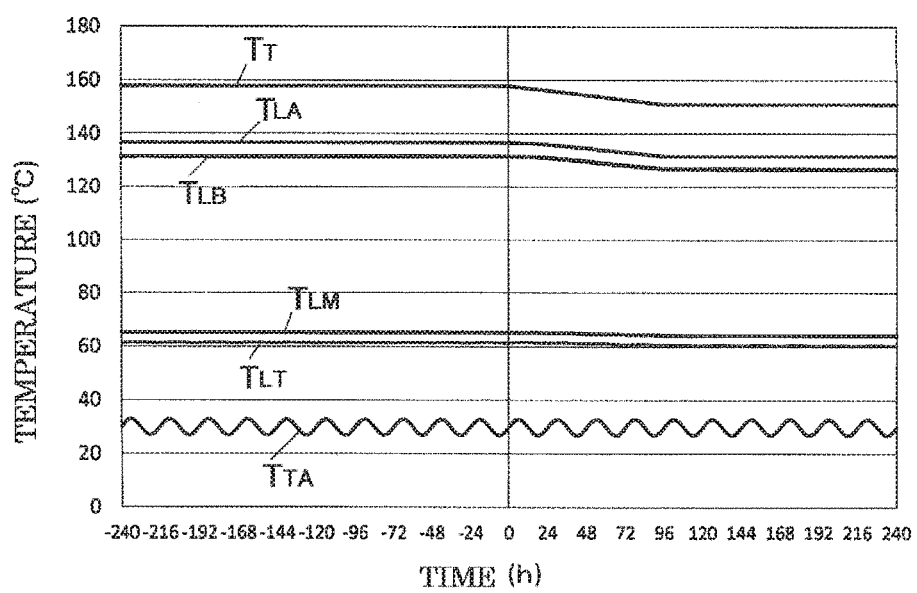
FIG. 20 is a graph illustrating time variation of temperatures at six measurement points illustrated in FIG. 3 before and after helium leakage in Case 1.
Figure 21:
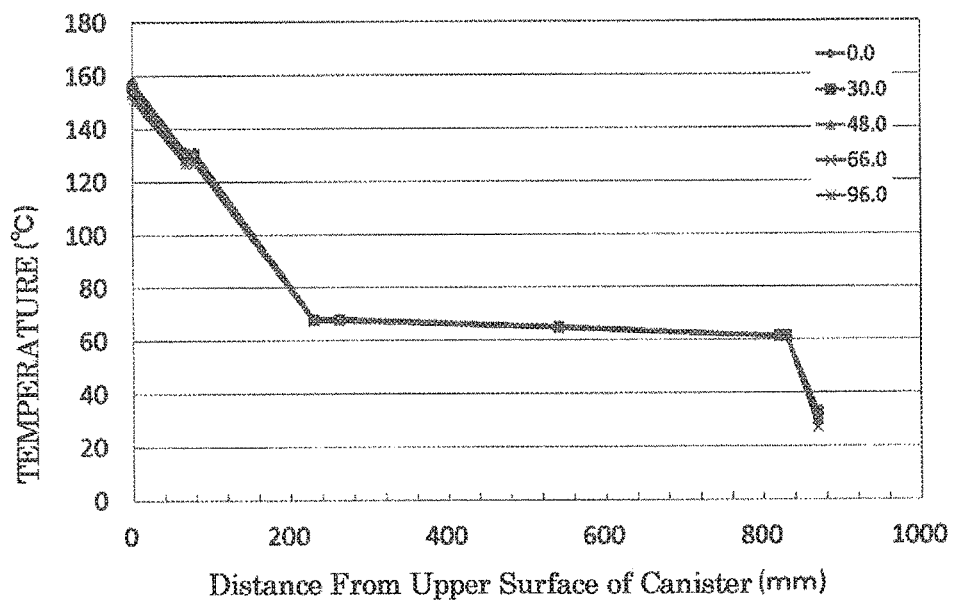
FIG. 21 is a graph illustrating temperature distribution from a point of measuring the concrete lid upper portion air temperature $T_{TA}$ to a point of measuring the canister top portion temperature $T_T$ in Case 1.

Analysis results are illustrated in FIGS. 20 and 21. From the analysis results, it is found that there is little temperature difference in a range of 200 mm to 800 mm from the upper surface of the canister, namely, inside the concrete 11 of the concrete lid. Therefore, any portion inside the concrete 11 may be suitable to be treated as the lid inner temperature $T_{LM}$.

Figure 22:
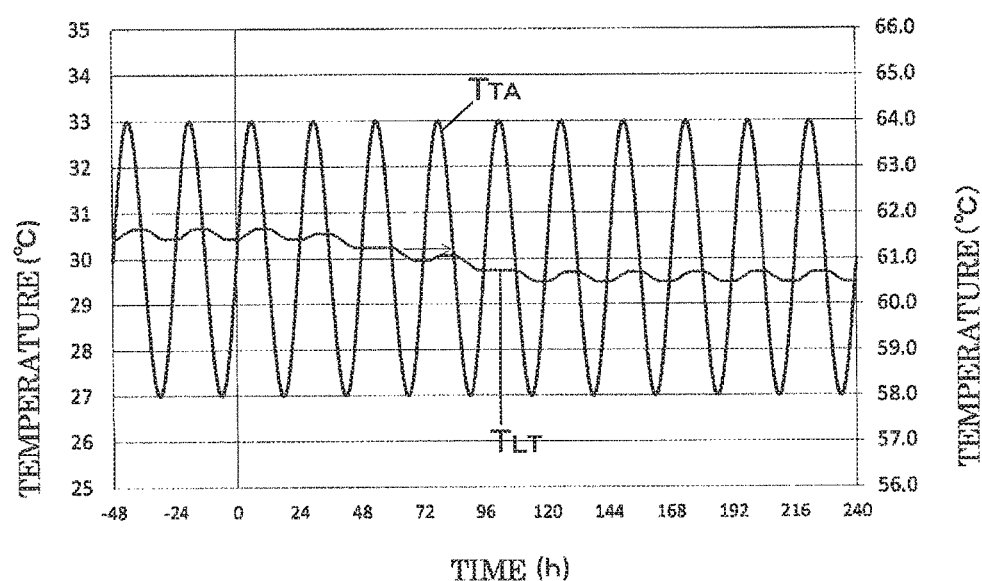
FIG. 22 is a graph illustrating a relation between the concrete lid upper portion temperature $T_{LT}$ and the concrete lid upper portion air temperature $T_{TA}$ before and after helium leakage in Case 1.

Additionally, as illustrated in FIG. 22, influence of the temperature fluctuation of the concrete lid upper portion air temperature $T_{TA}$ was observed in the concrete lid upper portion temperature $T_{LT}$, and also slight temperature decrease was observed after gas leakage start.

Furthermore, as illustrated in FIG. 23, according to the relation between the lid bottom portion temperature $T_{LB}$ and the lid inner temperature $T_{LM}$, same as the tendency observed in the tests, the lid bottom portion temperature $T_{LB}$ quickly followed fluctuation of the canister top portion temperature $T_T$ after gas leakage start while the lid inner temperature $T_{LM}$ insensitively followed the canister top portion temperature $T_T$, and a relative difference was generated between both temperatures.

Therefore, as illustrated in FIG. 24, when the value of $\delta(T_{LM}-T_{LB})$ is increased by monitoring and comparing the difference from the average value of the lid bottom portion temperature $T_{LB}$ and the difference from the average value of the lid inner temperature $T_{LM}$, it can be determined that leakage is occurring based on the fact that there is the significant fluctuation in the temperature differences.

Additionally, FIG. 25 illustrates comparison between $\delta(T_{LM}-T_{LB})$ and $\delta(T_{LM}-T_T)$. Judging from the results, it can be considered that the more the temperature information of the lid bottom portion temperature $T_{LB}$ close to the canister top portion temperature $T_T$ can be obtained, the more the detection sensitivity can be improved.

(4) Study on Improving Detection Sensitivity

Considering above, the inventor of the present invention made study on measurement positions by the one dimensional heat conduction analysis in order to obtain a setting position, namely, a measurement position of the first temperature sensor 21 at which higher sensitivity can be achieved.

In order to make the lid bottom portion temperature $T_{LB}$ closest to the temperature of the canister top portion temperature $T_T$ under the same analysis input conditions, a distance between the measurement position of the lid bottom portion temperature $T_{LB}$ and the canister top portion $1_T$ was set from 67 mm in FIG. 3 to 10 mm as illustrated in FIG. 2, and furthermore, a thickness of a glass wool 19 to the lower portion of the concrete was increased.

As a result, as illustrated in FIG. 28, it has been found that the lid bottom portion temperature $T_{LB}$ became a value almost same as the canister top portion temperature $T_T$. Judging from this fact, it can be considered that temperature information close to the canister top portion temperature $T_T$ can be obtained by setting the measurement point of the lid bottom portion temperature $T_{LB}$ close to the canister top portion $1_T$, and highly sensitive leakage detection can be achieved.

Furthermore, in the experiments, the metallic protection cover 20 formed of a metal plate having a thickness of 5 mm was provided at the tip of the bar-shaped thermometer 4. Additionally, the thermocouple 22 as the first temperature sensor was provided on a surface on the opposite of the surface facing the back surface of the metal plate 20, namely, the canister top portion $1_T$, and the back surface temperature $T_{LBI}$ at the lid bottom portion was measured. Since the metal plate 20 has high heat conductivity, it is found that the lid bottom portion temperature $T_{LB}$ and the back surface temperature $T_{LBI}$ of the metal plate at the lid bottom portion become almost the same values also from the result illustrated in FIG. 26.

Therefore, it is found that γ-rays may be prevented from directly being received from the canister top portion by arranging the thermocouple 22 on the back side of the metal plate 20 as the member that receives influence of the canister top portion temperature $T_T$ and measuring the back surface temperature $T_{LBI}$ of the metal plate.

What is claimed is:

1. A method for detecting gas leakage from a radioactive material sealed container, adapted to detect leakage of inactive gas from a metallic sealed container of the radioactive material sealed container that includes: the metallic sealed container configured to store and seal spent fuel and the inactive gas; and a non-sealed concrete-made storage container having a shielding function and configured to store the metallic sealed container, the method comprising:
   measuring a temperature at a top portion of the metallic sealed container, a temperature at a bottom portion of a lid portion of the concrete-made storage container facing the top portion of the metallic sealed container, or a temperature of a member existing between the bottom portion of the lid portion and the top portion of the metallic sealed container;
   also measuring an inner temperature of the lid portion of the concrete-made storage container; and
   estimating presence of leakage of the inactive gas by comparing the temperature at the top portion of the metallic sealed container with the inner temperature of the lid portion of the concrete-made storage container or comparing the inner temperature of the lid portion of the concrete-made storage container with the temperature at the bottom portion of the lid portion of the concrete-made storage container or the temperature of the member existing between the bottom portion of the lid portion and the top portion of the metallic sealed container.

2. The method for detecting gas leakage from a radioactive material sealed container according to claim 1, wherein a difference between the temperature at the top portion of the metallic sealed container and the inner temperature of the lid portion of the concrete-made storage container, or a difference between the temperature at the bottom portion of the lid portion of the concrete-made storage container or the temperature of the member existing between the bottom portion of the lid portion and the top portion of the metallic sealed container and the inner temperature of the lid portion of the concrete-made storage container is displayed in time series.

3. The method for detecting gas leakage from a radioactive material sealed container according to claim 1, wherein a temperature on a bottom surface of the lid portion of the concrete-made storage container is measured as the temperature at the bottom portion of the lid portion of the concrete-made storage container.

4. The method for detecting gas leakage from a radioactive material sealed container according to claim 1, wherein a temperature of a metal plate arranged at a position closer to the top portion of the metallic sealed container than the bottom surface of the lid portion of the concrete-made storage container is measured as the temperature of the member existing between the bottom portion of the lid portion of the concrete-made storage container and the top portion of the metallic sealed container.

5. An apparatus for detecting gas leakage from a radioactive material sealed container, adapted to detect leakage of inactive gas from a metallic sealed container of the radioactive material sealed container that includes: the metallic sealed container configured to store and seal spent fuel and the inactive gas; and a non-sealed concrete-made storage container having a shielding function and configured to store the metallic sealed container, the apparatus comprising:
   a first temperature sensor configured to measure a temperature at a top portion of the metallic sealed container, a temperature at a bottom portion of a lid portion of the concrete-made storage container facing the top portion of the metallic sealed container, or a temperature of a member existing between the bottom portion of the lid portion and the top portion of the metallic sealed container;
   a second temperature sensor configured to measure an inner temperature of the lid portion of the concrete-made storage container; and a gas leakage estimation unit configured to estimate presence of leakage of the inactive gas by comparing a temperature measured by the first temperature sensor with a temperature measured by the second temperature sensor.

6. The apparatus for detecting gas leakage from a radioactive material sealed container according to claim 5, further comprising a display device configured to display, in time series, a temperature difference between a temperature measured by the first temperature sensor and a temperature measured by the second temperature sensor.

7. The apparatus for detecting gas leakage from a radioactive material sealed container according to claim 5, wherein the first temperature sensor measures a temperature at the bottom portion of the lid portion of the concrete-made storage container.

8. The apparatus for detecting gas leakage from a radioactive material sealed container according to claim 5, wherein the first temperature sensor measures a temperature of a metal plate projecting toward the top portion of the metallic sealed container from a bottom surface of the lid portion of the concrete-made storage container and arranged at a position close to the top portion of the metallic sealed container.

9. The apparatus for detecting gas leakage from a radioactive material sealed container according to claim 8, wherein the first temperature sensor is arranged interposing the metal plate in a space with the top portion of the metallic sealed container by being provided on a back surface of the metal plate arranged at a position close to the top portion of the metallic sealed container, and is configured to measure a temperature of the back surface of the metal plate.

10. The apparatus for detecting gas leakage from a radioactive material sealed container according to claim 5, wherein the second temperature sensor measures a temperature of a concrete layer of the lid portion of the concrete-made storage container.

11. The apparatus for detecting gas leakage from a radioactive material sealed container according to claim 5, wherein the first temperature sensor and the second temperature sensor are arranged in a vicinity of a center position in a planar view of the lid portion of the concrete-made storage container and the top portion of the metallic sealed container.

12. The apparatus for detecting gas leakage from a radioactive material sealed container according to claim 5, wherein
the first temperature sensor and the second temperature sensor are thermocouples or thermistors, each held by a sensor holder having a shielding structure similar to the lid portion of the concrete-made storage container, and constitute a bar-shaped thermometer in which the first temperature sensor is provided on a surface of a metal plate at a tip portion and the second temperature sensor is embedded in a concrete layer, and
the second temperature sensor is arranged inside the lid portion of the concrete-made storage container, and the first temperature sensor is arranged in a position ranging from the bottom portion of the lid portion of the concrete-made storage container to the top portion of the metallic sealed container while a penetration hole is being closed by inserting the bar-shaped thermometer into the penetration hole provided at the lid portion of the concrete-made storage container and configured to communicate between the top portion of the metallic sealed container and outside of the concrete-made storage container.

13. The apparatus for detecting gas leakage from a radioactive material sealed container according to claim 12, wherein
a tip of the bar-shaped thermometer is made to project from the bottom portion of the lid portion of the concrete-made storage container toward the top portion of the metallic sealed container, and
the first temperature sensor is set close to the top portion of the metallic sealed container and measures a temperature at a position near the top portion of the metallic sealed container.

14. The apparatus for detecting gas leakage from a radioactive material sealed container according to claim 12, wherein the penetration hole at the lid portion of the concrete-made storage container is a tapered hole, the bar-shaped thermometer is tapered, and when the bar-shaped thermometer is inserted into the penetration hole, the lid portion of the concrete-made storage container closely contacts the bar-shaped thermometer.

15. The apparatus for detecting gas leakage from a radioactive material sealed container according to claim 12, wherein
the bar-shaped thermometer has a shielding structure, similar to the lid portion of the concrete-made storage container, formed by sequentially stacking a metal plate to be a lid, a concrete material, a metal plate, a heat insulator, and a metal plate to be a bottom and covered with a metal protection tube, and
the second temperature sensor is embedded in the concrete material and the first temperature sensor is fixed to a surface of the metal plate to be a bottom of the tip portion.

\* \* \* \* \*